US011580638B2

(12) United States Patent
Kobayashi et al.

(10) Patent No.: US 11,580,638 B2
(45) Date of Patent: Feb. 14, 2023

(54) ULTRASONIC IMAGE CONSTRUCTION METHOD, APPARATUS AND SIGNAL-PROCESSING METHOD

(71) Applicants: HONDA ELECTRONICS CO., LTD., Aichi (JP); NATIONAL UNIVERSITY CORPORATION TOYOHASHI UNIVERSITY OF TECHNOLOGY, Aichi (JP)

(72) Inventors: Kazuto Kobayashi, Aichi (JP); Naohiro Hozumi, Aichi (JP)

(73) Assignees: HONDA ELECTRONICS CO., LTD., Aichi (JP); NATIONAL UNIVERSITY CORPORATION TOYOHASHI UNIVERSITY OF TECHNOLOGY, Aichi (JP)

( * ) Notice: Subject to any disclaimer, the term of this patent is extended or adjusted under 35 U.S.C. 154(b) by 223 days.

(21) Appl. No.: 17/097,086

(22) Filed: Nov. 13, 2020

(65) Prior Publication Data
US 2021/0150709 A1 May 20, 2021

(30) Foreign Application Priority Data
Nov. 19, 2019 (JP) .............................. JP2019-208466

(51) Int. Cl.
*G06T 7/00* (2017.01)
*G06T 7/262* (2017.01)

(52) U.S. Cl.
CPC ............ *G06T 7/0012* (2013.01); *G06T 7/262* (2017.01); *G06T 2207/10132* (2013.01); *G06T 2207/20056* (2013.01)

(58) Field of Classification Search
None
See application file for complete search history.

(56) References Cited

FOREIGN PATENT DOCUMENTS

| CN | 109102552 A | * 12/2018 |
|---|---|---|
| JP | 2006-271765 | 10/2006 |
| JP | 6361001 | 7/2018 |

OTHER PUBLICATIONS

Machine translation of CN-109102552-A (Year: 2018).*

* cited by examiner

*Primary Examiner* — Vu Le
*Assistant Examiner* — Courtney Joan Nelson
(74) *Attorney, Agent, or Firm* — Clark & Brody LP

(57) ABSTRACT

This invention provides a signal-processing method that makes it possible to acquire, relatively easily and surely, a highly reliable normalized impulse-response signal without relying on the signal-correction processing after normalization. The signal-processing method of this invention includes a low-frequency extraction step, a high-frequency extraction step and a synthesizing step. In the low-frequency extraction step, only the low-frequency component is extracted from the spectrum of the first normalized signal NS1 obtained by normalizing the target signal $S_{tgt}$ in the time domain. In the high-frequency extraction step, only the high-frequency component is extracted from the spectrum of the second normalized signal NS2 obtained by normalizing the target signal $S_{tgt}$ in the frequency domain using the reference signal $S_{ref}$. In the synthesizing step, the low-frequency component, derived from the first normalized signal NS1, and the high-frequency component, derived from the second normalized signal NS2, are synthesized to obtain a normalized impulse-response signal NS.

18 Claims, 12 Drawing Sheets

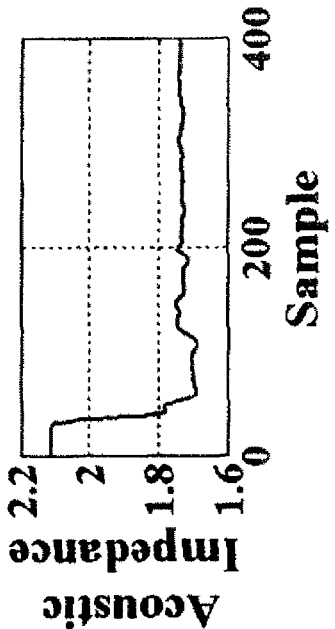
FIG. 12(a)
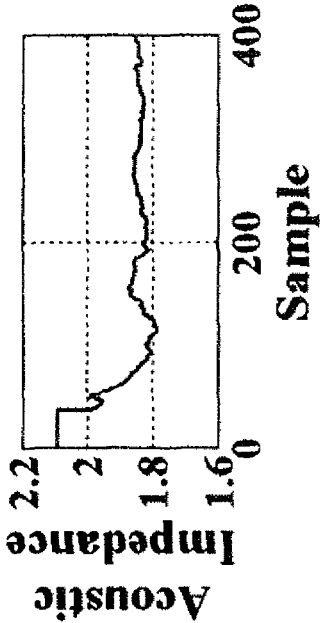
FIG. 12(b)
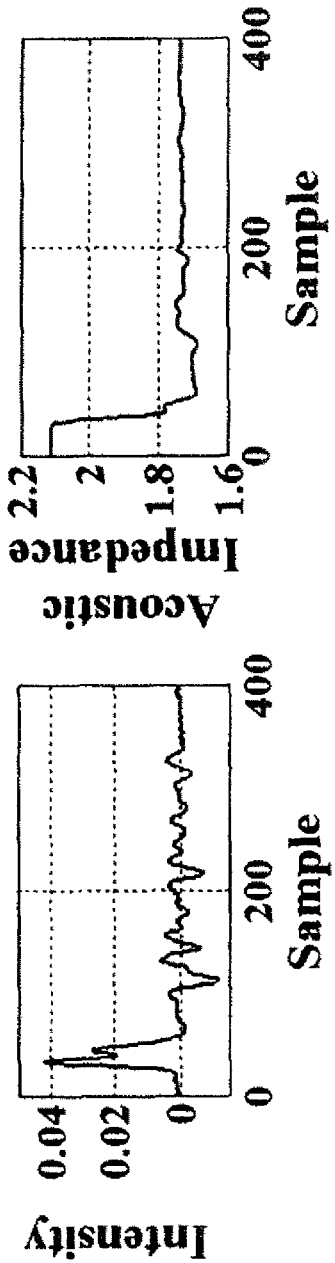
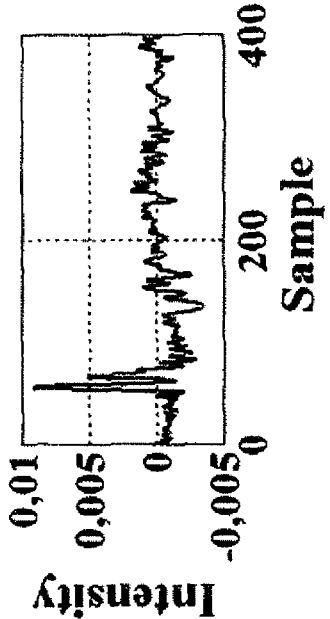
FIG. 12(c)
FIG. 12(d)

ULTRASONIC IMAGE CONSTRUCTION METHOD, APPARATUS AND SIGNAL-PROCESSING METHOD

TECHNICAL FIELD

This invention relates to, based on information obtained by using ultrasonic waves, a method for constructing a tomographic image of a biological tissue or the like represented by skin or the like, and relates to an apparatus and relates to a signal-processing method efficient in accurately constructing the tomographic image.

TECHNICAL BACKGROUND

The use of an ultrasonic B-mode echo image is a method widely used in the medical field, and many apparatuses for obtaining such an image have been proposed (see Patent Document 1). Briefly, an ultrasonic B-mode echo image is an image of a reflected-signal sequence of which an ultrasonic-wave incident on an object is reflected and returned. When it is assumed that the ultrasonic waves have traveled straight without having scattered, a reflection occurs due to the difference in the resistance value (characteristic-acoustic impedance) at the travel destination, the same as in the case of an electrical signal. Therefore, if the distribution of the characteristic-acoustic impedance is known, it is possible to estimate what kind of reflected signal-sequence has returned. In other words, if the distribution of the acoustic property is known, it is possible to estimate that which the B-mode image is supposed to have observed, conversely.

However, as for target objects of non-uniform thickness (depth) such as biological tissue or the like, the reflected waveform that penetrates and returns from such tissue reflects the result of ultrasonic-waves incident on the target object having undergone enormous scattering and absorption in various ways of traveling (the result of multiple reflection). For this reason, it is considered difficult to convert such a reflected waveform into acoustic properties such as a characteristic-acoustic impedance or the like, and this method has not been studied in the past. Also, since an ultrasonic B-mode echo image tends to be an image disturbed by speckle noise caused by multiple reflections of ultrasonic waves within a biological tissue, it is considered unsuitable for displaying the internal structure of such biological tissue with a high degree of accuracy. Therefore, of the conventional apparatus, a countermeasure such as an acoustic filter is required, although there is the problem that such a configuration is complicated.

Furthermore, regarding a normal ultrasonic-diagnostic apparatus that displays an ultrasonic B-mode echo image, at least information about the layered structure within a biological tissue such as skin or the like can be obtained. However, the obtained image is a reflected image of the interface between such structured layers of different characteristic-acoustic impedances, and such a reflected image is insufficient to perceive the internal structure of such biological tissue. Specifically, it is insufficient to perceive the difference in acoustic impedance within such biological tissue. In other words, it was easy to understand sensuously the reflected image obtained by the prior art whereof the interface of such layered structure existed. On the other hand, it was difficult to understand sensuously how the characteristic acoustic impedance of the intermediate region surrounded by such interface existed. Therefore, it has been desirable to construct an ultrasonic-tomographic image of a very thin target object to be measured, one having a layered structure in a fashion that makes it sensuously easy to understand such a layered structure based on the information obtained by using ultrasonic waves.

In light of such circumstances, the inventors of this invention have already proposed an improved ultrasonic-image construction apparatus (se e.g. Patent Document 2). This apparatus is configured so as to include a substrate having a known acoustic property, an ultrasonic transducer that transmits and receives ultrasonic waves via a base material, a computing unit, an image-constructing unit, and the like. In this device, a target substance and a reference substance having a known acoustic property are arranged in contact with a substrate having a known acoustic property. Then, in this state, an ultrasonic pulse is transmitted, an ultrasonic wave is incident on the target substance and on the reference substance via the substrate, and response signals (target signal and reference signal) are received from the target substance and the reference substance respectively. Next, the target signal is deconvoluted (that is, normalized) in the frequency domain using the reference signal, thus obtaining a normalized impulse-response signal. Based on this normalized impulse-response signal, calculation is performed to estimate the acoustic-property distribution in the depth direction (specifically, the characteristic acoustic-impedance distribution) in consideration of the influence of multiple reflections. Since the reflection coefficient inside the soft tissue is small, the acoustic property distribution in the depth direction can be estimated by a simpler calculation when the influence of multiple reflections is small enough to be ignored. Then, image data is constructed based on the obtained acoustic property distribution in the depth direction, so that a desired ultrasonic-tomographic image is obtained.

PRIOR ARTS

Patent Documents

[Patent Document 1] Japanese Published Unexamined Patent Application No. 2006-271765
[Patent Document 2] Japanese Patent Publication No. 6361001

OUTLINE OF THE INVENTION

Problems to be Solved by the Invention

By the way, in the case of the above-described conventional apparatus, the noise of the low-frequency spurious component is ridden on the "normalized impulse response signal" obtained through the calculation of the deconvolution process, and therefore the baseline is unstable, and an error is generated. It is inevitable that the acoustic property value estimated based on such an impulse-response signal may include a larger error. Therefore, there was the disadvantage that a desired ultrasonic-tomographic image cannot be obtained unless the acoustic property distribution is obtained after the normalized impulse-response signal is corrected by some calculation to remove the influence of the low-frequency spurious component.

This invention has been achieved in light of the above-mentioned problems, and the first objective of this invention is to provide an ultrasonic-image construction method and an ultrasonic-image construction apparatus, which make it possible relatively to construct easily and surely a stable ultrasonic-tomographic image of a very thin target substance having a fine internal structure without relying on the signal-correction process after the normalization.

A second objective of this invention is to provide a signal processing method which makes it possible to relatively easily and surely acquire a highly-reliable normalized impulse response signal without relying on the signal-correction process after normalization.

Means for Solving the Problems

To solve the above problems, the inventors of this invention have earnestly conducted research, and have confirmed the following findings. That is, when the response signal is deconvoluted in the conventional apparatus, usually a calculation is performed in a fashion that the target signal and the reference signal are once converted into the frequency domain to divide the target signal by the reference signal and then to return to the time domain again (see FIG. 14). In this case, to avoid discontinuity of the time-domain waveform, the waveform that is cut out in the time domain is adjusted so that both ends of the waveform show the same value. Specifically, as shown in FIG. 14, a window function is applied such that both ends smoothly approach zero, thus producing the waveform such that both ends gradually approach zero. As such, the high-frequency component, which the window function itself has, is reduced. In this process, on the other hand, the intensity of the waveform before being cut out is modulated by the window function. Since the intensity modulation in the time domain is a convolution that is integral in the frequency domain, the unnecessary spectral component is generated. The waveform originally has a small low-frequency component, but the unnecessary low-frequency component (that is, the low-frequency spurious component) generated by the window function is superimposed on the entire region. As a result, the low-frequency component of the restored waveform that has been deconvoluted to acquire the impulse response signal will be destabilized. Also, FIG. 15(a) shows a waveform that has been normalized in the frequency domain and then returned to the time domain in which the unnecessary low-frequency spurious component is superimposed over the entire area. FIG. 15(b) is also of a time-domain waveform showing a reference example of which the low-frequency spurious component is not superimposed but normalized relatively correctly.

Based on such findings, the present inventors do not directly use the signal obtained by normalizing the target signal in the frequency domain as the "normalized impulse-response signal," but we invented a way to remove the unnecessary spectral component with a large error from the "normalized impulse-response signal" and on the other hand to replace the removed spectral component with less error obtained by normalizing the target signal by another method. In other words, the inventors invented a way to extract the high-spectrum component with a small error from the impulse-response signal obtained by normalizing the target signal in the frequency domain and to extract the spectrum component with a small error from the impulse-response signal obtained by normalizing the target signal with another method, so as to synthesize them together, thus making it a complementary "normalized impulse-response signal." Then, the inventors of this invention earnestly continued with further researches based on such an idea and came up with the following means of solution.

The first aspect of this invention refers to an ultrasonic-image construction method, characterized in comprising: a transmitting/receiving step in which an ultrasonic pulse is transmitted through the substrate in the state whereof the target substance and the reference substance are in contact with the substrate and in which the target signal from the target substance and the reference signal from the reference substance are received; a signal-normalization step to extract only the low-frequency component from the first normalized signal obtained by normalizing the target signal in the time domain, and to extract only the high-frequency component from the second normalized signal obtained by normalizing the target signal in the frequency domain using the reference signal, so as to synthesize the low-frequency component derived from the first normalized signal with the high-frequency component derived from the second normalized signal, thus obtaining the normalized impulse signal; a characteristic acoustic-impedance distribution-estimation step to estimate sequentially the characteristic acoustic-impedance distribution in the target substance from the front side to the back side in the depth direction according to the normalized impulse-response signal; and an image-construction step to construct the image data of the acoustic property image according to the characteristic acoustic-impedance distribution in the depth direction.

Therefore, according to the first aspect of this invention, the first normalized signal obtained by normalizing the target signal in the time domain includes the high-frequency component with a lower resolution and only the useful low-frequency component with a small error, so that such an unnecessary high-frequency component is removed from the signal. Also, the second normalized signal obtained by normalizing the target signal in the frequency domain includes the low-frequency component and the low-frequency spurious component with relatively large errors. However, by extracting only the useful high-frequency component with a relatively small error, the unnecessary low-frequency component and the low-frequency spurious component are removed from the above signal. Therefore, combining the useful low-frequency component derived from the first normalized signal and the useful high-frequency component derived from the second normalized signal complements the inaccurate parts of the two components, thus making it possible relatively to acquire easily and surely a highly reliable normalized-impulse response signal. Further, according to the first aspect of this invention, the signal-correction processing after normalization, which has been conventionally indispensable to obtain a desired ultrasonic-tomographic image, becomes unnecessary.

The second aspect of this invention refers to an ultrasonic-image-construction apparatus, characterized in comprising: a substrate; an ultrasonic transducer to transmit an ultrasonic pulse through the substrate in a state where the target substance and the reference substance are in contact with the substrate and which can receive the target signal from the target substance and receive the reference signal from the reference substance; a signal-normalization means to extract only the low-frequency component from the first normalized signal obtained by normalizing the target signal in the time domain and to extract only the high-frequency component from the second normalized signal obtained by normalizing the target signal in the frequency domain using the reference signal, so as to synthesize the low-frequency component derived from the first normalized signal with the high-frequency component derived from the second normalized signal, thus obtaining a normalized impulse-response signal; a characteristic acoustic-impedance distribution-estimation means to estimate sequentially the characteristic acoustic-impedance distribution in the target substance from the front side to the back side in the depth direction according to the normalized impulse response signal; and an image-construction means to construct the image data of the acoustic property image according to the acoustic-impedance distribution in the depth direction obtained by the characteristic acoustic-impedance distribution-estimation means.

The third aspect of this invention refers to a signal-processing method for acquiring a normalized impulse-response signal based on a target signal obtained by pulse-wave irradiation against a target substance and a reference signal obtained by pulse-wave irradiation against a reference substance, characterized in comprising: a low-frequency extraction step to extract only the low-frequency component from the spectrum of the first normalized signal obtained by normalizing the target signal in the time domain; a high-frequency extraction step to extract only the high-frequency component from the spectrum of the second normalized signal obtained by normalizing the target signal in the frequency domain using the reference signal; and a synthesizing step to synthesize the low-frequency component derived from the first normalized signal and the high-frequency component derived from the second normalized signal, thus acquiring a normalized impulse-response signal.

It is possible that before performing the high-frequency extraction step, a waveform is formed by applying a window function to the reference signal and to the target signal. As such, the waveform that is cut out from each of the above signals is adjusted and formed, so that both ends of the waveform show the same value, thus making it possible to convert each of the above signals into the frequency domain without difficulty.

It is also possible that in the low-frequency extraction step, the first normalized signal after extracting only the low-frequency component is converted into the frequency domain by Fourier transform.

It is also possible that in the synthesizing step, the low-frequency component derived from the first normalized signal and the high-frequency component derived from the second normalized signal are synthesized in the frequency domain and thereon the acquired normalized impulse-response signal is converted into the time domain from the frequency domain by inverse Fourier transform.

It is also possible that in the low-frequency extraction step, down-sampling processing is performed after removing the high-frequency component from the reference signal and from the target signal, respectively, thereafter, the target signal, after the down-sampling process, is normalized in the time domain using the reference signal after the down-sampling process. As such, as compared to the conventional signal-processing method in which the normalization is done in the time domain without performing the down-sampling process, the number of data samples is reduced, and the computation labor required for the normalization is reduced, thus making it possible to save computation time.

It is further possible that in the low-frequency extraction step, in the low frequency extraction step, the source signal is obtained by removing the low-frequency component and the high-frequency component from the spectrum of the second normalized signal, thereon such an source signal is converted in the time domain for a peak detection, thereafter a base signal having an impulse is generated around the peak, thus normalizing the target signal in the time domain using the base signal instead of the reference signal. As such, as compared to the conventional signal processing method in which the normalization is done in the time domain without generating the base signal or the like, the computation labor required for the normalization is reduced, thus making it possible to save the computation time.

Effect of the Invention

As described above in detail, according to the first and the second aspects of this invention, it is possible to construct relatively easily and surely a stable ultrasonic-tomographic image of a very thin target substance having a fine internal structure without relying on signal-correction processing after the normalization. Also, it is possible to construct relatively easily and surely an ultrasonic-tomographic image that makes it possible easily and accurately to observe and evaluate the internal structure of cultured cells and of biological soft tissues such as skin or the like. According to the third aspect of this invention, it is possible to provide a signal-processing method for acquiring a highly reliable normalized impulse-response signal relatively easily and surely without relying on signal-correction processing after the normalization. Using this method also makes it possible accurately to construct, for example, the above-mentioned ultrasonic-tomographic image.

BRIEF DESCRIPTION OF THE DRAWINGS

FIG. 12(a) is a graph showing the intensity of the normalized impulse-response signal obtained by the signal-processing method as the embodiment of this invention. FIG. 12(b) is a graph showing the characteristic acoustic-impedance calculated from the above response signal.

FIG. 12(c) is a graph showing the intensity of the normalized impulse-response signal obtained by the conventional signal-processing method for normalizing only in the frequency domain. FIG. 12(d) is a graph showing the characteristic acoustic impedance calculated from the above response signal.

MODES FOR CARRYING OUT THE INVENTION

Hereinafter, an embodiment of which the ultrasonic-image construction method and the apparatus of this invention is described in detail with reference to FIGS. 1 to 12.

Figure 1:
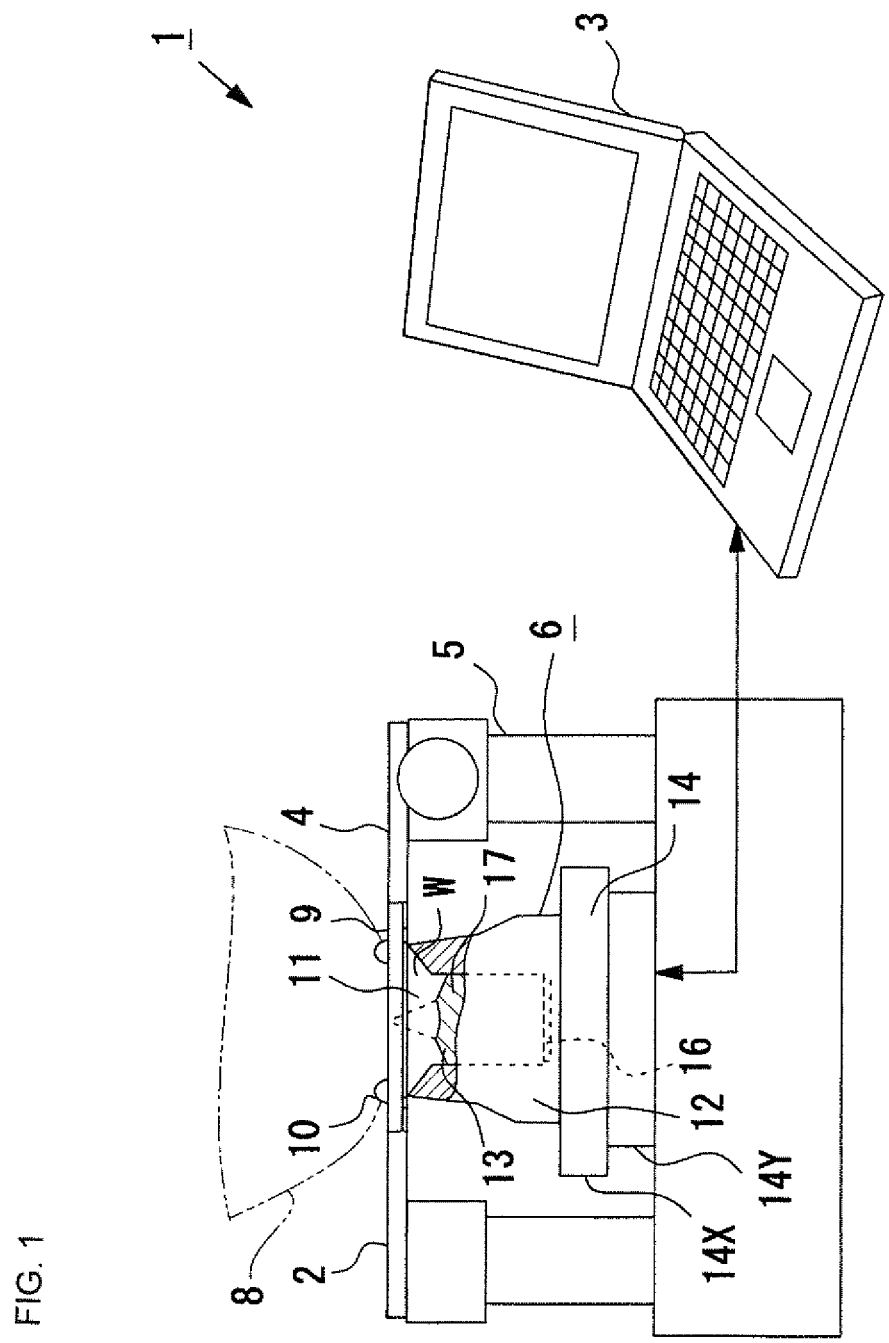
FIG. 1 is a schematic-configuration drawing showing the ultrasonic-image construction apparatus as an embodiment of this invention.

FIG. 1 is a schematic-configuration diagram showing the ultrasonic-image construction apparatus 1 as the embodiment of this invention. As shown in FIG. 1, the ultrasonic-image construction apparatus 1 is an apparatus for observing, diagnosing, etc. the skin 8 using ultrasonic waves and includes a pulse-excitation ultrasonic microscope 2 and a personal computer (PC) 3.

The pulse-excitation-type ultrasonic microscope 2 includes a microscope main body 5, having a stage 4, and an ultrasonic probe 6 provided below the stage 4. The ultrasonic probe 6 of the pulse-excitation-type ultrasonic microscope 2 is electrically connected to the PC 3.

The stage 4 of this embodiment is configured so as to be movable in a horizontal direction (i.e., in the X direction and Y direction) manually by an operator. A resin plate 9 is fastened onto the stage 4 to be attached in contact with the object to be measured. The target to be measured is a soft biological tissue (specifically, skin tissue: skin 8) including blood vessels extending in a direction substantially parallel to the tissue surface. In this embodiment, the measurement or the like is performed by pressing the human skin 8 directly against the resin plate 9. The resin plate 9, as a substrate having known acoustic properties, is a flat plate-shaped member that is able to transmit ultrasonic waves and is made of a material harder than the skin 8 as the object to be measured. When a member having such a shape and hardness is used as the substrate, the skin 8 as the object to be measured can be properly placed in close contact with such a substrate. As such, the characteristic acoustic-impedance distribution in the depth direction can be accurately estimated, thus improving the accuracy of image-construction. The embodiment of this invention employs a polystyrene plate having a thickness of 1.4 mm. Of course, it is acceptable to employ a plate material made of a resin other than polystyrene.

A reference member 10, as a reference substance, is previously set on the upper surface of the resin plate 9 that is to be contacted with the skin 8. The reference member 10 has a known acoustic property different from that of the resin plate 9. In the embodiment of this invention, for example, the reference member 10 is formed by adhering an acrylic resin (acrylic adhesive). However, it is certainly not limited to this. A material other than the resin material (for example, a glass material, a metal material, a ceramic material, etc.) may be used as the reference member 10, as long as it can be placed in contact with the reference member 10. Alternatively, instead of placing such a reference member 10, water or the like, for example, is to be present so as to be in contact with the upper surface of the resin plate 9, thus using it as a reference substance. By setting the reference member 10 on the resin plate 9 in advance, the impulse-response information of the ultrasonic waveform incident on the reference member 10 can be accurately and stably acquired without depending on changes in the environment in which the apparatus is set.

An ultrasonic probe 6 includes a probe main-body 12 having a storage 11 that can store an ultrasonic-transmission medium W such as water or the like at its tip, and an ultrasonic transducer 13 arranged at a substantially central portion of the probe main-body 12, and an X-Y stage 14 for two-dimensionally scanning the probe main-body 12 along the planer direction of the stage 4. The upper part of the storage 11 of the probe main-body 12 is open, and the ultrasonic probe 6 is installed below the stage 4, with the opening side of the storage 11 being turned upward.

The ultrasonic transducer 13 consists of for example, a thin film-piezoelectric element 16 made of zinc oxide, and an acoustic lens 17 made of sapphire rod. The ultrasonic transducer 13 is pulse-excited to irradiate the ultrasonic waves to the skin 8 and to the reference member 10 from the lower-surface side of the resin plate 9. The ultrasonic waves irradiated by the ultrasonic transducer 13 are converged in a conical shape via the ultrasonic-transmission medium W of the storage 11 so as to be focused on the upper surface of the resin plate 9 (in the vicinity of the surface of the skin 8). The embodiment of this invention employs an ultrasonic transducer 13 having a diameter of 1.8 mm, a focal length of 3.2 mm, a center frequency of 80 MHz, and a bandwidth of 50 to 105 MHz (−6 dB).

Figure 2:
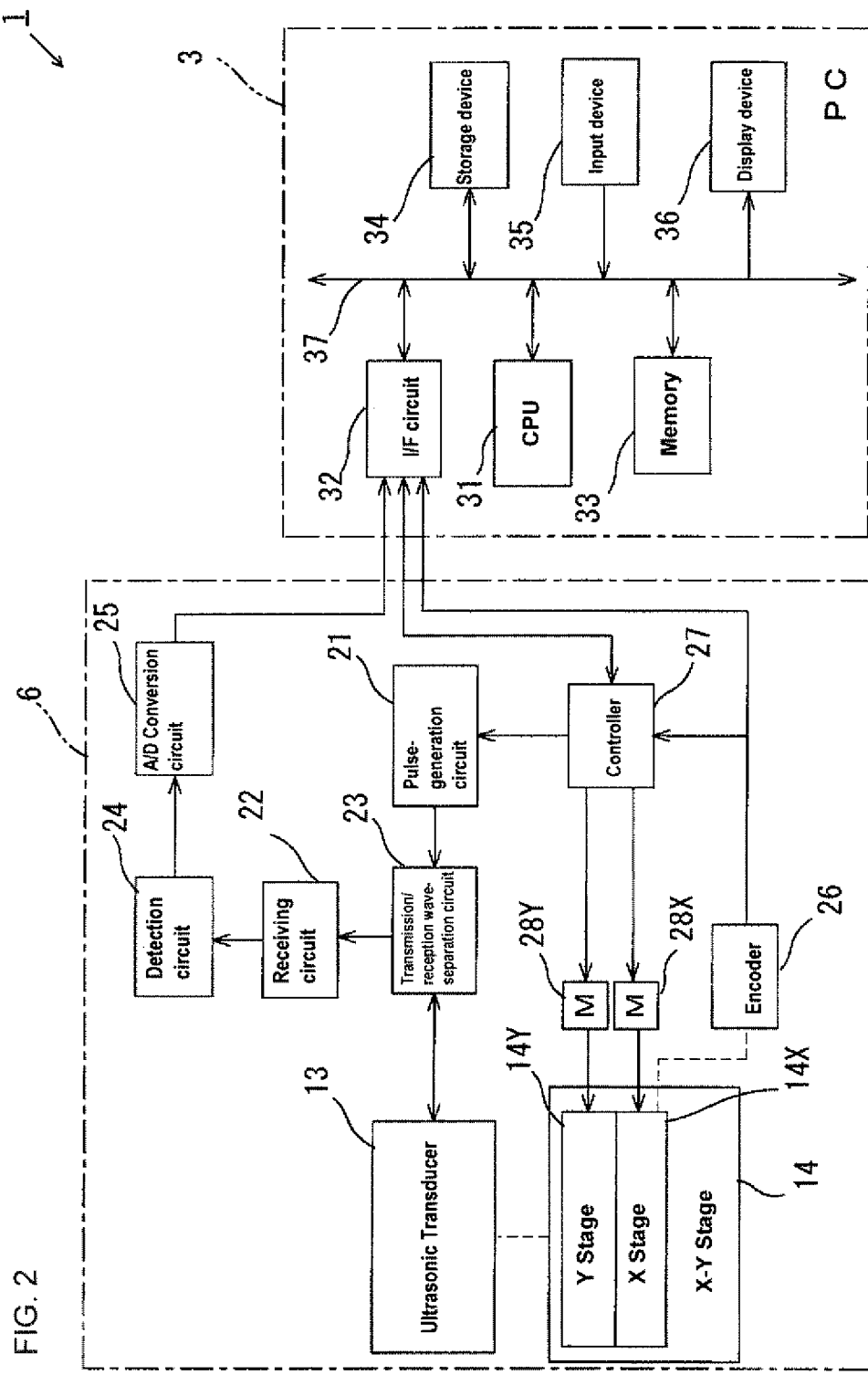
FIG. 2 is a block drawing showing the electrical configuration of the ultrasonic-image construction apparatus as the embodiment of this invention.

FIG. 2 is a block diagram showing the electrical configuration of the ultrasonic-image-construction apparatus 1 as the embodiment of this invention.

As shown in FIG. 2, the ultrasonic probe 6 includes an ultrasonic transducer 13, an X-Y stage 14, a pulse-generation circuit 21, a receiving circuit 22, a transmission/reception wave-separation circuit 23, a detection circuit 24, an A/D conversion circuit 25, an encoder 26, and a controller 27.

The X-Y stage 14, as the scanning means, includes an X stage 14X and a Y stage 14Y for two-dimensionally scanning the irradiation point of the ultrasonic waves, and also includes motors 28X and 28Y for driving the stages 14X and 14Y, respectively. A stepping motor or a linear motor is used for these motors 28A and 28Y.

A controller 27 is connected to each of the motors 28X and 28Y, which are driven in response to a drive-signal of the controller 27. Once these motors 28X and 28Y are being driven, the X stage 14X is continuously scanned (continuously fed), and the Y stage 14Y is controlled to be intermittently fed, thus making it possible to realize high-speed scanning of the X-Y stage 14.

Further, according to the embodiment of this invention, the encoder 26 is provided in response to the X-stage 14X. Then, the scanning position of the X-stage 14X is detected by the encoder 26. Specifically, when the scanning range is divided into 300×300 measurement points (pixels), a single scan in the X direction (horizontal direction) is divided into 300. Then, the position of each measurement point is detected by the encoder 26 and is taken into the PC3. The PC 3 generates a drive-control signal in synchronization with the output of the encoder 26 and then supplies the drive-control signal to the controller 27. The controller 27 drives the motor 28X on the basis of this drive-control signal. Also, the controller 27 drives the motor 28Y at the time when the scanning of one line in the X direction is completed on the basis of the output signal of the encoder 26, so as to move the Y stage 14Y by one pixel in the Y direction.

Further, the controller 27 generates a trigger signal in synchronization with the drive-control signal and supplies it to the pulse-generation circuit 21. As such, the pulse-generation circuit 21 generates an excitation pulse at the timing of synchronization with the trigger signal. As a result of the excitation pulse being supplied to the ultrasonic transducer 13 via the transmission/reception wave-separation circuit 23, ultrasonic waves are irradiated from the ultrasonic transducer 13.

Figure 3:
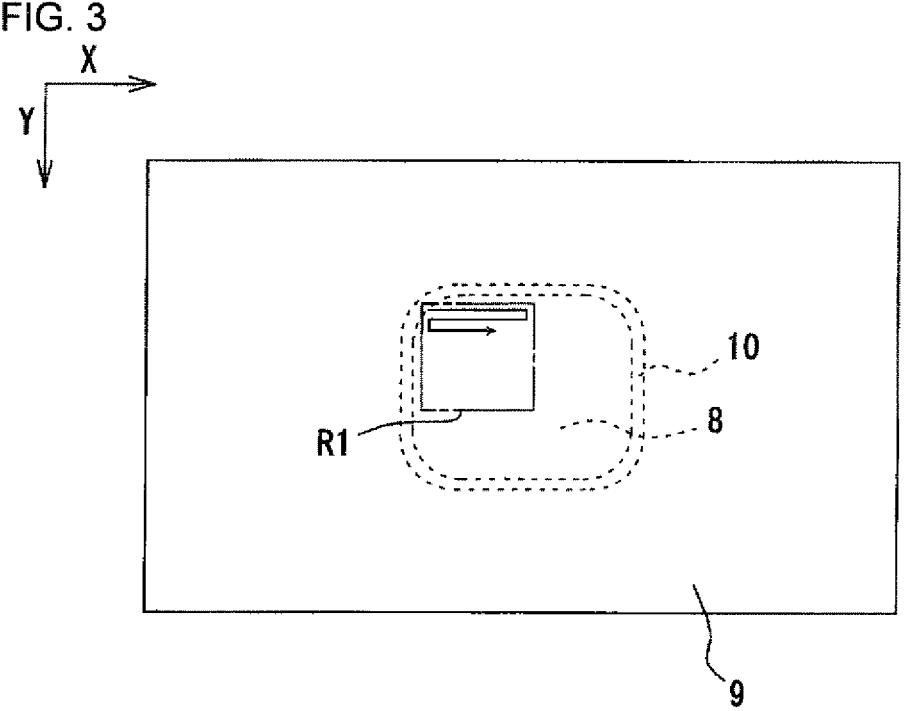
FIG. 3 is a schematic drawing showing an example of the ultrasonic-scanning range according to the movement of the X-Y stage.

FIG. 3 shows an example of the ultrasonic-scanning range R1 in association with the movement of the X-Y stage 14. In this example, the reference member 10 is provided so as to encompass the region to be in contact with the skin 8. Then, with the human skin 8 being pressed against the region, scanning begins at a position where the reference member 10 is located. Then, as indicated by the arrows in FIG. 3, two-dimensional scanning is sequentially done in the X direction and Y direction along the surface of the skin 8.

The thin-film-piezoelectric element 16 of the ultrasonic transducer 13 is an ultrasonic transducer that both transmits and receives the ultrasonic waves and also converts ultrasonic waves (reflected waves) reflected by the skin 8 into electric signals. Then, the reflected-wave signal is supplied to the receiving circuit 22 via the transmission/reception wave-separation circuit 23. The receiving circuit 22 comprises a signal-amplification circuit to amplify the reflected-wave signal and to output the reflected-wave signal to the detection circuit 24.

The detection circuit 24 is a circuit for detecting the reflected-wave signal from the skin 8 and includes a gate circuit (not shown in the drawings). The detection circuit 24 as the embodiment of this invention extracts the reflected-wave signals received by the ultrasonic transducer, that is, the reflected-wave signals (i.e., the target signals) from the skin 8 and the reflected-wave signals (i.e., the reference signals) from the reference member 10. Then, the reflected wave signals extracted by the detection circuit 24 is supplied to the A/D conversion circuit 25 for A/D conversion, thus being transferred to the PC3.

The PC 3 comprises a CPU31 (central-processing unit), an I/F circuit 32, a memory 33, a storage device 34, an input device 35, and a display device 36, which are all connected to each other via a bus 37.

The CPU31 executes a control program, using the memory 33, and integrally controls the entire system. The control program includes a program for controlling two-dimensional scanning by the X-Y stage 14, a program for converting the reflected-signal-sequence data that is the source of the ultrasonic B-mode echo image into a characteristic acoustic-impedance image, and a program for displaying the characteristic acoustic-impedance image, and other programs. Also, besides the CPU31, a Digital Signal Processor (DSP), for example, may be provided to execute a part of the signal processing that is supposed to be performed by the CPU31.

The I/F circuit 32 is an interface (specifically, a USB interface) for sending and receiving signals to and from the ultrasonic probe 6. The I/F circuit 32 has a function to output a control signal (drive-control signal to the controller 27) to the ultrasonic probe 6 and to input transfer data from the ultrasonic probe 6 (data transferred from the A/D conversion circuit 25, or the like.). When sending and receiving the signal to and from the ultrasonic probe 6, it is not limited to the physical interface, as described above, but a wireless interface may also be used.

The display device 36 is, for example, a monitor display such as a liquid crystal, plasma or organic electroluminescence (EL) or the like. The display device 36 can be used regardless of whether it is a color display or a monochrome display, but it is desirable to use a color display. The display device 36 is used for displaying a characteristic acoustic-impedance image of the surface layer of the skin 8 and for displaying an input screen for various settings.

The input device 35 is a user-inputting interface for a touch panel, a mouse, a keyboard, a pointing device and the like and is used for inputting requests, instructions and parameters by the user.

The storage device 34 is a hard-disk drive such as a magnetic-disk device, an optical-disk device or the like to store various control programs and various data. The memory 33 includes random-access memory (RAM) and read-only memory (ROM) to store the reflected waveform and the characteristic acoustic impedance of the reference member 10 acquired in advance for ultrasonic measurement. The CPU31 transfers programs and data from the storage device 34 to the memory 33, according to the instructions from the input device 35, and sequentially executes them. The program executed by the CPU31 may be a program stored in a storage medium such as a memory card, a flexible disk, an optical disk or a program downloaded via a communication medium. At the time of the CPU31 executing the program, they (any one of such storage medium) are installed in the storage device 34 and used.

According to the ultrasonic-image-construction device 1 as the embodiment of this invention, a method for constructing an acoustic-impedance image from a reflected-signal sequence that is a source of the ultrasonic B-mode echo image is now hereinafter described.

According to the ultrasonic-image-construction apparatus 1, when constructing an acoustic-impedance image, an ultrasonic pulse is first transmitted through the resin plate 9 in contact with the skin 8 and with the reference member 10. Then, the target signal, which is the response signal from the skin 8, and the reference signal that is the response signal from the reference member 10, are received (transmission/reception step). Next, after acquiring a "normalized-impulse-response signal" according to these response signals (signal-normalization step), the characteristic acoustic-impedance distribution within the skin 8 is sequentially estimated from the front side to the back side in the depth direction according to the response signal (characteristic acoustic-impedance-distribution-estimation step).

Also, to perform such an estimation, assuming that in the calculation step the lossless micro-transmission paths 51 of different acoustic impedances are connected in the depth direction to form an assembly of micro-transmission paths 51 within the target substance, a calculation to estimate the an acoustic property (i.e. characteristic acoustic-impedance distribution) in the depth direction of the transmission path is done by sequentially repeating the process of estimating the acoustic impedance of the micro-transmission path 51 adjacent to the back side based on the estimated result of the acoustic impedance of the micro-transmission path 51 on the front side. Such a calculation is executed based on a predetermined algorithm having been stored in the memory 33.

This algorithm is an algorithm for estimating the acoustic-impedance distribution in the depth direction by using a reflected-signal sequence that is the basis of an ultrasonic B-mode echo image. This algorithm refers to the principle of the time-domain reflection-measurement method (Time Domain Reflectometry method, i.e., TDR) and is also an algorithm for converting a reflected-signal sequence that is the source of the ultrasonic B-mode echo image into an acoustic-impedance image in the depth direction through an analysis of the time-frequency domain in consideration of the multiple reflections within the skin tissue. This is specifically described, below.

Figure 4A:
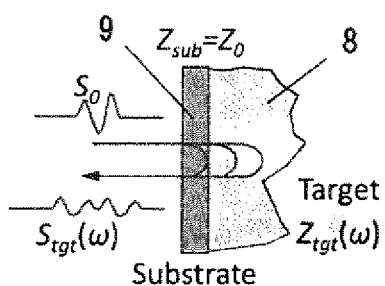
FIG. 4(a) is an explanatory drawing about the acquisition of a reflected waveform from the target substance during the actual measurement.
Figure 4B:
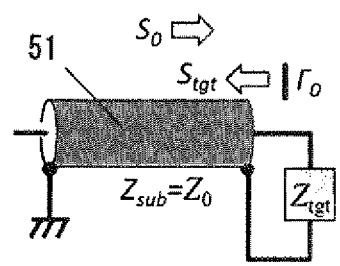
FIG. 4(b) is an explanatory drawing about the acquisition of a reflected waveform when the target substance is regarded as a micro-transmission path.

FIG. 4(*a*) is a drawing explaining the acquisition of the reflected waveform from a target substance when the actual measurement is done. FIG. 4(*b*) is a drawing explaining the acquisition of a reflected waveform when assuming that the target substance is a micro-transmission path 51. FIG. 5(*a*) is a drawing explaining the acquisition of a reflected waveform from a reference substance when the actual measurement is done. FIG. 5(*b*) is a drawing explaining the acquisition of the reflected waveform when assuming that the reference substance is a micro-transmission path 51.

Firstly, as shown in FIG. 4(*a*), the ultrasonic transducer 13 is activated, causing an ultrasonic-convergent beam of a depth of focus sufficient for the target substance to be transmitted through the resin plate 9 as the base substrate. Then, a convergent beam of ultrasonic waves is incident onto the skin 8 as the target substance, and a reflected waveform therefrom is thus acquired. The impulse response $\Gamma_0(\omega)$ of such convergent beam of ultrasonic waves at this time is expressed by the following Formula 1 from the incident wave $S_0$ and the reflected wave $S_{tgt}(\omega)$ from the skin 8 using the Fourier transform.

[Formula 1]

$$\Gamma_0(\omega) = \frac{S_{tgt}(\omega)}{S_0} \qquad (1)$$

In this case, it is necessary to obtain a reflected waveform, too, from the reference member 10 that has a known and uniform characteristic acoustic impedance as well as being of sufficient thickness compared to the skin 8 as the target substance. The reflected wave $S_{ref}(\omega)$ from the reference member 10 is expressed by the following Formula 2 using the characteristic acoustic impedance $Z_{ref}$ of the reference member 10 and the characteristic acoustic impedance $Z_0$ of the resin plate 9.

[Formula 2]

$$S_{ref}(\omega) = \frac{Z_{ref} - Z_0}{Z_{ref} + Z_0} S_0 \qquad (2)$$

Further, the impulse response $\Gamma_0(\omega)$ from the skin 8 as the target substance is expressed by the following Formula 3. However, since the impulse response $\Gamma_0(\omega)$ includes reflections generated from a plurality of interfaces behind the tissue of the skin 8, the impulse response $\Gamma_0(\omega)$ has frequency characteristics. Thus, the normalized impulse-response information is obtained from the impulse-response information of the ultrasonic waveform incident onto the reference substance, and the impulse-response information of the ultrasonic waveform incident onto the measurement object is obtained by the referenced Formulae, above. However, according to the embodiment of this invention, a more accurate "normalized impulse-response signal" is acquired by using the algorithm of the signal-normalization step described below, and subsequent computations are performed based on the acquired "normalized impulse-response signal."

[Formula 3]

$$\Gamma_0(\omega) = \frac{Z_{ref} + Z_0}{Z_{ref} - Z_0} \cdot \frac{S_{tgt}(\omega)}{S_{ref}(\omega)} \qquad (3)$$

Figure 6:
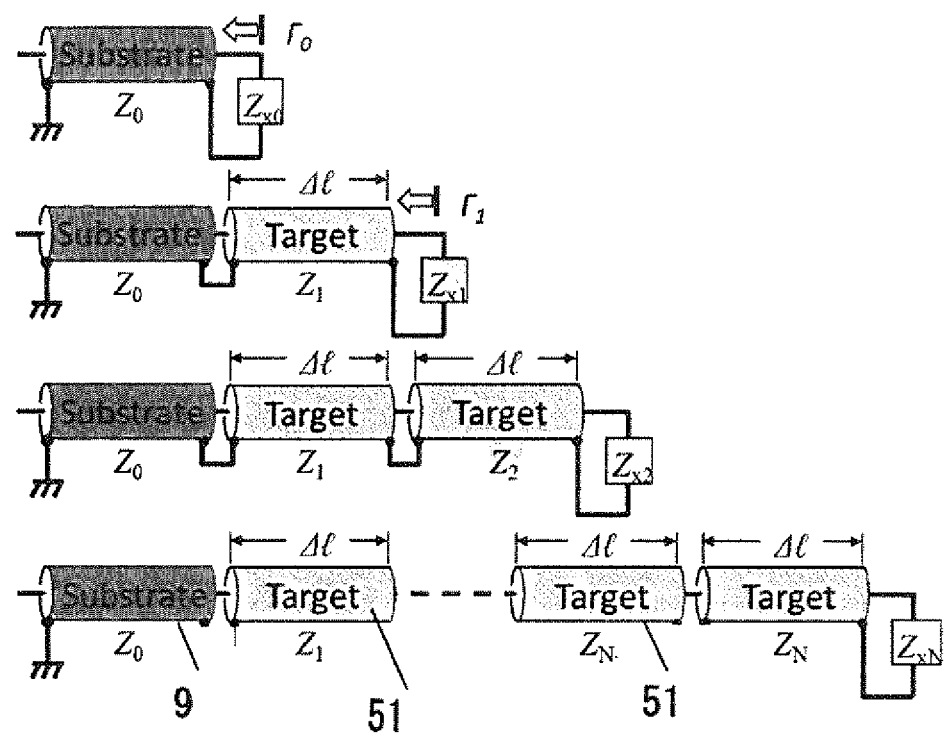
FIG. 6 is a diagram conceptually showing how the characteristic impedance of each micro-transmission path is estimated.

Here, FIG. 6 is a drawing conceptually showing the state in which the characteristic impedances $Z_1, Z_2, \ldots Z_n$ of each micro-transmission path 51 are estimated, in order, from the micro-transmission path 51 in contact with the resin plate 9. As shown in this drawing, the characteristic impedances $Z_1, Z_2 \ldots Z_n$ of each micro-transmission path are estimated sequentially from the micro-transmission path 51 in contact with the resin plate 9 in the depth direction.

Figure 7:
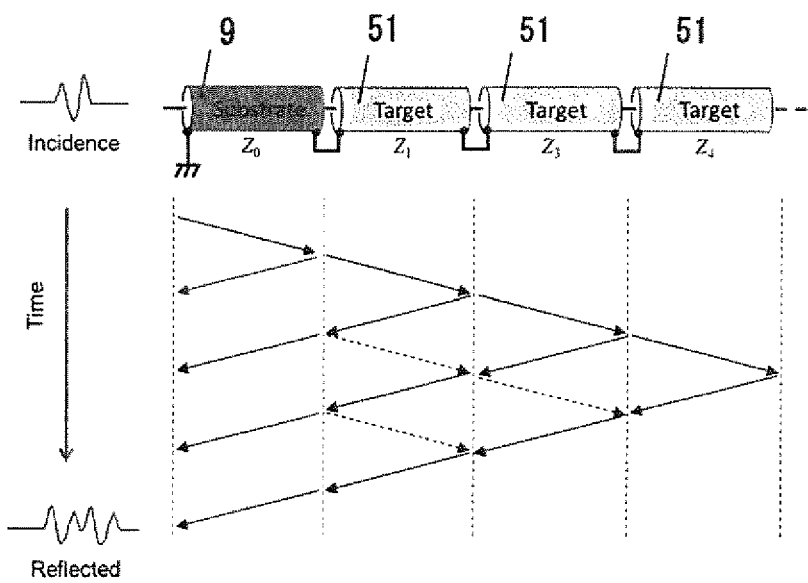
FIG. 7 is a drawing conceptually showing the influence of multiple reflections.

FIG. 7 is a drawing conceptually showing the effect of multiple reflections. The following Formula 4 represents $g_0(t)$ obtained by inverse Fourier transform of the impulse response $\Gamma_0(\omega)$, but the first term is not affected by such multiple reflections (see FIG. 7). Therefore, the characteristic impedance Z1 of the micro-transmission path 51 in contact with the resin plate 9 can be estimated from the value of the first term, as shown in the following Formula 5.

[Formula 4]

$$g_0(t) = IFT(\Gamma_0(\omega)) \qquad (4)$$

[Formula 5]

$$Z_1 = \frac{1 + g_0(t_0)}{1 - g_0(t_0)} Z_0 \qquad (5)$$

The characteristic acoustic impedance $Z_{x0}$ of the skin 8 in the frequency domain is expressed by the following Formula 6 by using $\Gamma_0$.

[Formula 6]

$$Z_{x0} = \frac{1 + \Gamma_0}{1 - \Gamma_0} Z_0 \qquad (6)$$

$Z_{x0}$ is also expressed by the following Formula 7 by using the impulse response $\Gamma_1$ from further behind.

[Formula 7]

$$Z_{x0} = \frac{1 + \Gamma_1 e^{-2\gamma \Delta l}}{1 - \Gamma_1 e^{-2\gamma \Delta l}} Z_1 \qquad (7)$$

Hereinafter, as described in the following Formulae 8 and 9, γ is the propagation constant, α is the attenuation constant, ß is the phase constant and f is frequency. However, in the conversion algorithm of the embodiment of this invention, it is assumed that $\alpha=0$, and that the sonic speed of all of the micro-transmission paths 51 of the skin 8 is c=1600 (W/s).

[Formula 8]
$$\gamma = \alpha + j\beta \tag{8}$$

[Formula 9]
$$\beta = \frac{2\pi f}{c} \tag{9}$$

Also, here the distance $\Delta l$ of each micro-transmission path 51 is expressed by the following Formula 10, and the sonic speed is assumed to be c=1600 (m/s). The distance $\Delta t$ corresponds to one point of the sampling interval of the reflected waveform from the skin 8 ($\Delta t=2$ (ns) in this embodiment).

[Formula 10]
$$\Delta l = c\Delta t \tag{10}$$

Then, based on the above formula, the impulse response $\Gamma_1$ from the micro-transmission path 51 that is located deeper can be obtained (see the following Formula 11). In other words, the value of $\Gamma_1$ at the end-point of $Z_1$ can be estimated based on the values of $Z_{x0}$ and $Z_1$.

[Formula 11]
$$\Gamma_1 = \frac{Z_{x0} - Z_1}{Z_{x0} + Z_1} e^{2\gamma \Delta l} \tag{11}$$

Formula 12, below, expresses $g_1(t)$ that is obtained by the inverse Fourier transform of the impulse response $\Gamma_1(\omega)$, and the first term is not affected by multiple reflections. Accordingly, it is possible to estimate, based on the value of the first term, the characteristic impedance $Z_2$ of the further deeper micro-transmission path 51 adjacent to the micro-transmission path 51, and it is possible to estimate $Z_{x1}$, $\Gamma_2(\omega)$. (See Formulae 13, 14 and 15).

[Formula 12]
$$g_1(t) = IFT(\Gamma_1(\omega)) \tag{12}$$

[Formula 13]
$$Z_2 = \frac{1 + g_1(t_0)}{1 - g_1(t_0)} Z_1 \tag{13}$$

[Formula 14]
$$Z_{x1} = \frac{1 + \Gamma_1}{1 - \Gamma_1} Z_1 = \frac{1 + \Gamma_2 e^{-2\gamma \Delta l}}{1 - \Gamma_2 e^{-2\gamma \Delta l}} Z_2 \tag{14}$$

[Formula 15]
$$\Gamma_2 = \frac{Z_{x1} - Z_2}{Z_{x1} + Z_2} e^{2\gamma \Delta l} \tag{15}$$

By repeating this process, the characteristic impedances (characteristic acoustic impedances) $Z_1, Z_2, \ldots Z_n$ of each micro-transmission path 51 can be estimated. According to the characteristic acoustic-impedance-estimation calculation, multiple reflections being propagated are taken into consideration, but since the multiple reflections are small within the actual body, the above calculation can be realized even if ignoring the multiple reflections.

According to the algorithm as the embodiment of this invention, the characteristic acoustic-impedance-estimation step as described above is performed to estimate the characteristic acoustic-impedance distribution in the depth direction. As such, the reflected-signal sequence that is the source of the B-mode echo image is finally converted into a characteristic acoustic-impedance image.

Figure 8:
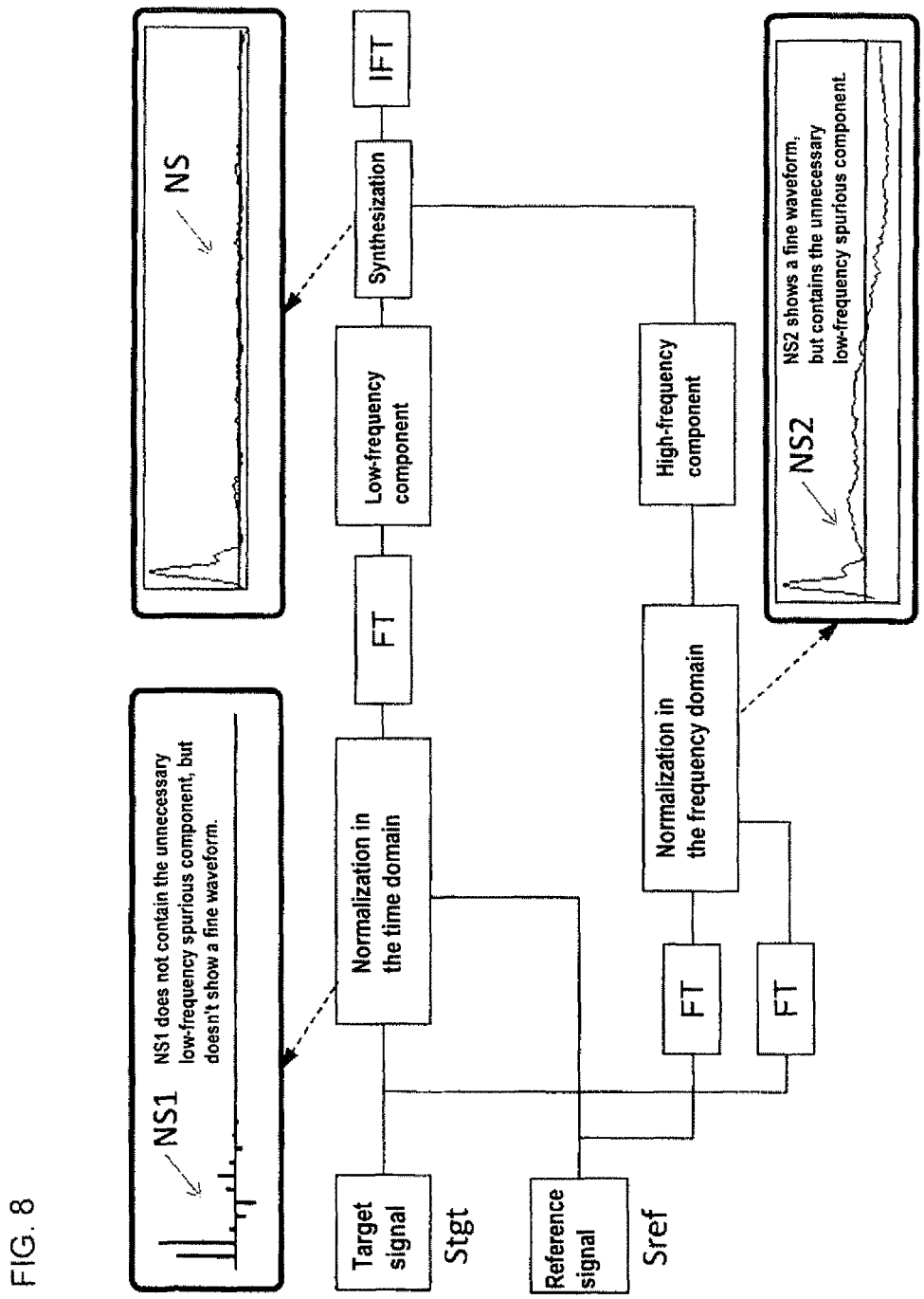
FIG. 8 is a diagram conceptually showing the signal-processing method as the embodiment of this invention.

Also, according to the algorithm of the embodiment of this invention, a predetermined-signal-normalization step, below, is further done prior to the characteristic acoustic-impedance-estimation step as described above. FIG. 8 is a diagram conceptually explaining the signal-normalization step as the embodiment of this invention. In this signal-normalization step, the target signal $S_{tgt}$ is normalized in the frequency domain using the reference signal $S_{ref}$ with a conventional method, and only the high-frequency component is extracted from the obtained second-normalized signal NS2. On the other hand, the target-signal $S_{tgt}$ is normalized in the time domain, and the obtained first-normalized signal NS1 is converted into the frequency domain to extract only the low-frequency component. Then, the low-frequency component derived from the first normalized signal NS1 and the high-frequency component derived from the second normalized signal NS2 are combined in the frequency domain to acquire the normalized impulse-response signal NS. After that, the impulse-response signal NS in the above-mentioned normalized-frequency domain is converted into the time domain, thus making it possible to remove the unnecessary low-frequency spurious component. The necessary low-frequency component and the unnecessary low-frequency spurious component are distinguished by the number of waves emerging in one period of the fundamental wave. The useful low-frequency component herein refers to the low-frequency component composed of, for example, five or more waves emerging in one cycle of the fundamental wave. On the other hand, the unnecessary low-frequency spurious component refers to the low-frequency component composed of, for example, fewer than five waves emerging in one cycle of the fundamental wave. By the way, the high-frequency component means the component composed of, for example, 20 or more waves emerging in one cycle of the fundamental wave.

Figure 9:
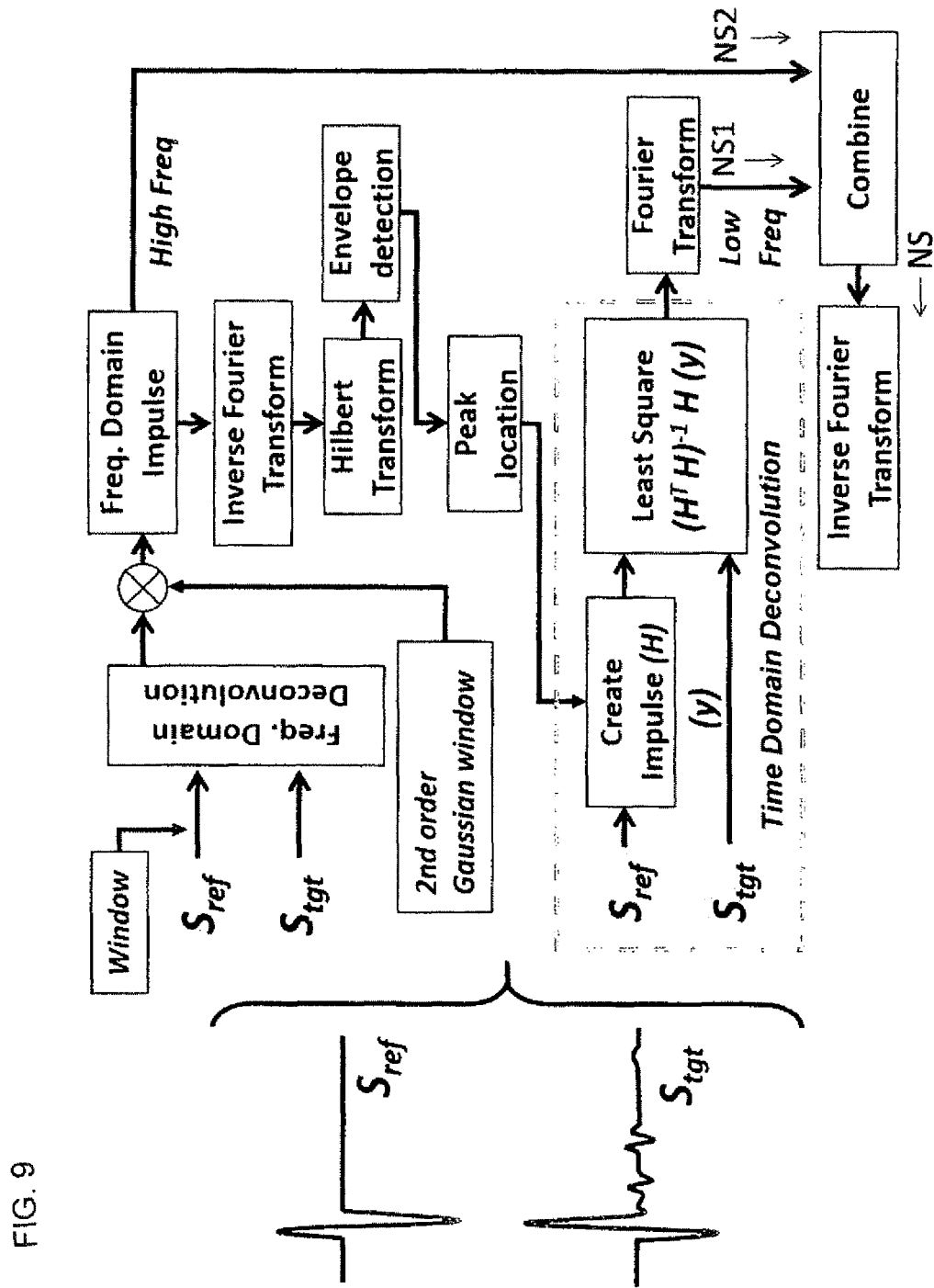
FIG. 9 is a diagram specifically showing the signal-processing method as an embodiment of this invention.

FIG. 9 is the diagram for more specifically explaining the signal-normalization step as the embodiment of this invention and is hereinafter described in detail based on this diagram.

In this signal-normalization step, to obtain the second normalized signal NS2, firstly a window function, in which both ends smoothly approach zero, is applied to the target-signal $S_{tgt}$ and to the reference-signal $S_{ref}$. As a result, a waveform is cut out from each signal in each time-domain. The waveform of the signal cut-out in this way is adjusted and shaped so that both ends have identical value. Next, the target-signal $S_{tgt}$ and the reference-signal $S_{ref}$ are Fourier-transformed to convert them into signals in the frequency domain, and then the target-signal $S_{tgt}$ is normalized (reverse-convolution process) in the frequency domain using the reference-signal $S_{ref}$, thus obtaining the second normalized signal NS2. The second normalized signal NS2 at this stage contains a fine waveform (the high-frequency component), but the NS2 also contains the unnecessary low-frequency spurious component (see the lower-right waveform in FIG. 8). Further, the second normalized signal NS2 is output via, for example, a bandpass filter, so as to extract only the useful high-frequency component contained in the signal. That is, the second normalized signal NS2 in the frequency domain, where the unnecessary low-frequency spurious component and the low-frequency component have been removed, is to be obtained.

According to this signal-normalization step, the following is performed to obtain the first normalized signal NS1 by normalization in the time domain. That is, instead of using the reference signal $S_{ref}$ itself which is a response signal from the reference substance, a predetermined base signal is generated from the reference signal $S_{ref}$ and used, thus conducting the normalization of the time domain. Specifically, the low-frequency component and the high-frequency component are removed from the spectrum of the above second normalized signal NS2 so as to make it the source signal. Then, such a source signal is converted into the time domain by the inverse Fourier transform. Next, the signal is subjected to a process corresponding to envelope detection using the Hilbert transform to detect the envelope of the signal, and then the peak position of each envelope is detected. After that, the signal is shifted around the detected-peak area at appropriate intervals in the direction of the time axis, so as to generate some basal signals having impulses. Furthermore, the least-squares method is used to compute the highly intense and optimum combination of these multiple base signals, thus making it linearly coupled. The signal obtained as a result of this linear coupling (conveniently referred to as "coupled-base signal") is used instead of the reference signal $S_{ref}$ to normalize the target signal $S_{tgt}$ in the time domain (reverse-convolution process). This processing makes it possible to obtain the first normalized signal NS1. Since the number of expected impulses is limited in such a coupled-base signal (in other words, only highly-intensive impulses are included), the obtained first normalized signal NS1 shows less time resolution due to the lack of the high-frequency component. However, since such a coupled-base signal does not contain the unnecessary low-frequency spurious component, the baseline of the first normalized signal NS1 is nearly horizontal and relatively stable (see the waveform on the upper left in FIG. 8). Next, the above-mentioned first normalized signal NS1 is Fourier transformed to be converted into the first normalized signal NS1 in the frequency domain and to be output through a low-pass filter in which a predetermined threshold value is set, thus extracting only the useful low-frequency component.

Furthermore, in this signal-normalization step, the useful low-frequency component derived from the first normalized signal NS1, and the useful high-frequency component derived from the second normalized signal NS2, are synthesized in the frequency domain to acquire the normalized impulse-response signal NS (see the waveform on the upper right in FIG. 8). Then, finally, the impulse-response signal NS in the above-mentioned normalized frequency domain is inverse-Fourier-transformed, thus obtaining the impulse-response signal NS in the normalized frequency domain.

Next, to construct the characteristic acoustic-impedance image by the ultrasonic-image-construction apparatus 1 as the embodiment of this invention, the arithmetic processing executed by the CPU31 that is a processor will be described with reference to the flowchart of FIG. 10.

First, the human skin 8 to be measured (for example, the skin 8 of the neck in which thick blood vessels (i.e. cervical veins, cervical arteries) are present relatively at shallow depth) is closely placed against the upper surface of the resin plate 9. In this state, firstly the ultrasonic probe 6 is activated to perform the initial operation. That is, by operating the controller 27 based on the instructions from the CPU31, the motors 28X and 28Y are driven to move the X-Y stage 14, so that the reference member 10 is irradiated with the ultrasonic waves at a certain position.

Figure 5A:
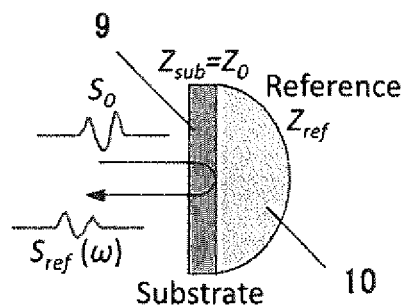
FIG. 5(a) is an explanatory drawing about the acquisition of a reflected waveform from the reference substance during the actual measurement.
Figure 5B:
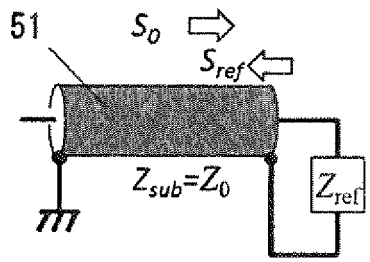
FIG. 5(b) is an explanatory drawing about the acquisition of a reflected waveform when the reference substance is regarded as a micro-transmission path.

At this time, once the excitation pulse is supplied to the ultrasonic transducer 13 based on the instructions from the CPU31, the ultrasonic waves $S_0$ is irradiated onto the reference member 10, as shown in FIG. 5(a). Then, the reference signal $S_{ref}(\omega)$, which is the reflected wave, passes through the receiving circuit 22 and is detected by the detection circuit 24. Then, the CPU31, as the reflected-wave acquisition means, acquires the digital data converted by the A/D conversion circuit 25 via the I/F circuit 32, and such obtained data is stored in the memory 33 as the impulse-response data (i.e. the reference data) of the ultrasonic waveform from the reference member 10 (step S100).

Thereafter, the motors 28X and 28Y are driven by the controller 27 according to the instructions from the CPU31, and then the two-dimensional scanning by the X-Y stage 14 is started. The CPU31 acquires the coordinate data of the measurement point based on the output of the encoder 26 (step S110).

As shown in FIG. 4(a), an excitation pulse is sent to the transducer 13 based on instruction from the CPU31. Then, the ultrasonic wave $S_0$ is irradiated onto the skin 8. Thereby, the target signal $S_{tgt}(\omega)$, as the reflected wave, is detected by the detection circuit 24 via the receiving circuit 22. The CPU31, as the reflected-wave-acquisition means, then acquires the digital data converted by the A/D conversion circuit 25 via the I/F circuit 32, and such digital data is associated with the coordinated data as the impulse-response data (i.e. the target-signal data) of the ultrasonic waveform from the skin 8 and then stored in the memory 33 (step S120).

Next, the CPU31, as the signal-normalization means, executes the algorithm of the signal-normalization step as described above to acquire the normalized impulse-response signal NS (step S125).

Next, the CPU31, as the characteristic acoustic-impedance-estimation means, executes the computation of the characteristic acoustic-impedance estimation-distribution step with reference to the principle of the TDR method, among the above algorithm, using the data of the normalized impulse-response signal NS. Then, the CPU31 sequentially estimates the characteristic acoustic impedance in the depth direction at the measurement point on the skin 8 from the front side to the back side in the depth direction, thus storing the estimated results in the memory 33 in association with the coordinate data (step S130).

After that, the CPU31, as the image-constructing means, performs image processing for constructing a characteristic acoustic-impedance image (tomographic image) based on the estimated result of the characteristic acoustic-impedance distribution in the depth direction (step S140). Specifically, the CPU31 performs color-modulation processing based on the estimated result of the characteristic acoustic-impedance distribution and constructs image-data displayed in different colors according to the magnitude of the characteristic-acoustic impedance and stores the image data in the memory 33.

Then, the CPU31 completes the processing of all of the measurement points and determines whether the image data has been acquired from all of the measurement points or not (step S150). If all of the data has not been acquired (step S150), then "NO" appears on the display, and the CPU31 returns to step S110 and repeats the processes of steps S110 to S140. If all of the data has been acquired (step S150), then "YES" appears on the display, and the CPU31 proceeds to the next step S160.

Figure 10:
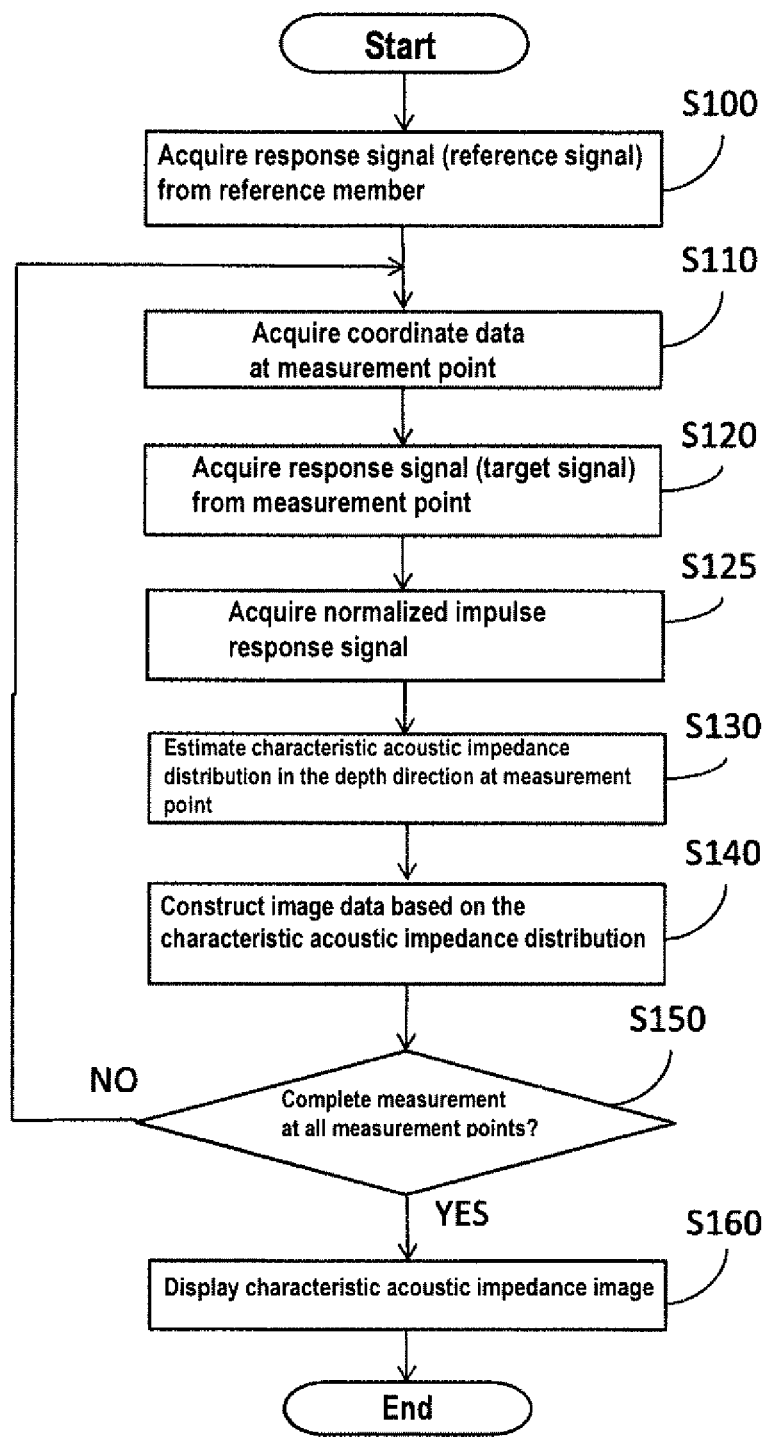
FIG. 10 is a flow-chart for explaining the computation process about the construction of the characteristic acoustic-impedance image.

Then, the CPU31 transfers the data to the display device 36 and displays the characteristic acoustic-impedance image (tomographic image) that is present on a predetermined straight line (step S160), thus completing the processing, as shown in FIG. 10. After such a series of processes, a characteristic acoustic-impedance image (tomographic image), which is color-coded according to the magnitude of the characteristic acoustic impedance at the skin 8, is displayed.

Figure 11A:
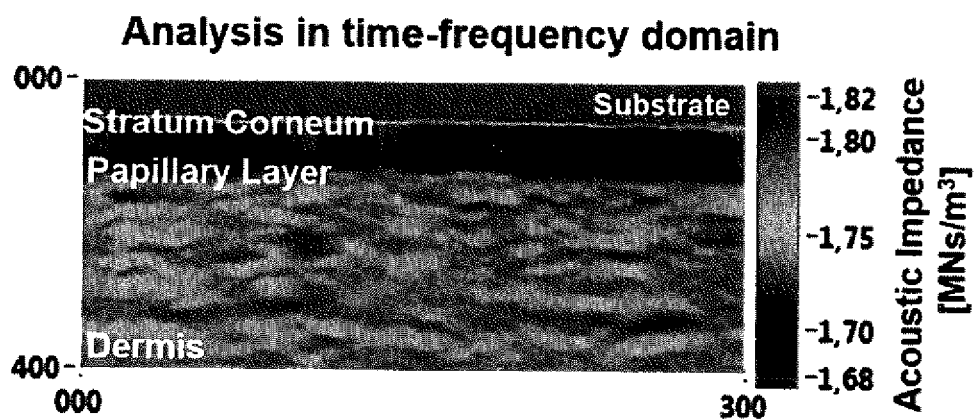
FIG. 11(a) is an acoustic-impedance image obtained by estimating the characteristic acoustic-impedance distribution of the skin through the signal-processing method as the embodiment of this invention.
Figure 11B:
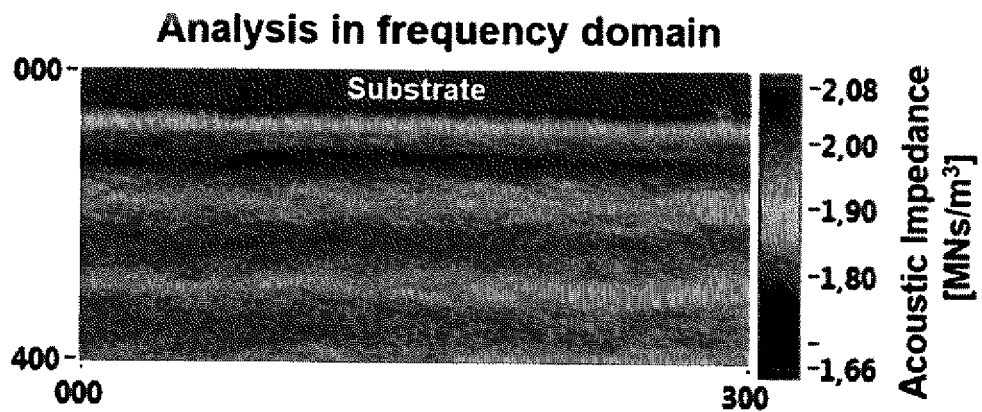
FIG. 11(b) is an acoustic-impedance image obtained by estimating the characteristic acoustic-impedance distribution of the skin through the conventional signal-processing method for normalizing only in the frequency domain.

Here, FIG. 11(a) is the acoustic-impedance image obtained by estimating the characteristic acoustic-impedance distribution of the skin 8 through the signal-processing method as the embodiment of this invention, and FIG. 11(b) is the acoustic-impedance image obtained by estimating the characteristic acoustic-impedance distribution of the skin 8 through the conventional signal-processing method for performing the normalization only in the frequency domain.

As shown in FIG. 11 (a), in the acoustic-impedance image by the method of this embodiment, the details of the skin structure in the dermis region and some layers could be clearly seen. In addition, the region between the stratum corneum and the papillary layer showed a lower-characteristic acoustic-impedance value than that of the dermis region. This corresponded to the fact that the dermis region, which has a high-characteristic acoustic-impedance value, is made up of structurally hard elastin and collagen, while the lower region of the papillary layer is filled with cells such as keratinocytes or the like.

To the contrary, as shown in FIG. 11 (b), the acoustic-impedance image by the conventional method did not decode the difference in these structures and details, and differences in each layer could not be clearly seen. Therefore, one reason was anticipated in a way that the normalized impulse-response signal obtained by the conventional method contains noise of the high-frequency component.

FIG. 12(a) is a graph showing the intensity (time-dependent reflection coefficient) of the normalized impulse-response signal obtained by the signal-processing method as the embodiment of this invention. FIG. 12(b) is a graph showing the characteristic-acoustic impedance calculated from the above response signal. FIG. 12(c) is a graph showing the intensity of the normalized impulse-response signal obtained by the conventional signal-processing method for normalizing only in the frequency domain. FIG. 12(d) is a graph showing the characteristic-acoustic impedance calculated from the above response signal.

When comparing the signal waveform of FIG. 12 (a) with the signal waveform of FIG. 12 (c), it was found that the former had a better profile than the latter. That is, in the latter case, the low-frequency spurious component is superimposed over the entire signal waveform, and the signal baseline is undulating and unstable. On the other hand, in the former case, such a superposition of the low-frequency spurious component was not seen, and the baseline was almost horizontal and stable. Also, in the latter case, since noise of the high-frequency component was included in the entire signal waveform, it is difficult to perceive accurately the waveform in a region where the absolute value of the reflection coefficient is small. On the other hand, in the former case, since the noise of the high-frequency component is barely included, it is possible to perceive the waveform relatively accurately in the region where the absolute value of the reflection coefficient is small. Therefore, it was concluded that the profile of the characteristic-acoustic impedance shown in FIG. 12 (b) is better and more reliable than that of the characteristic-acoustic impedance shown in FIG. 12 (d).

Therefore, the embodiment of this invention realizes the following effects.

(1) The ultrasonic-image-construction apparatus 1 as the embodiment of this invention is characterized in that the predetermined signal-normalization step, described above, is performed. That is, according to this signal-normalization step, only the low-frequency component is extracted from the first normalized signal NS1 obtained by normalizing the target signal $S_{tgt}$ in the time domain. In addition, only the high-frequency component is extracted from the second normalized signal NS2 obtained by normalizing the target signal $S_{tgt}$ in the frequency domain using the reference signal $S_{ref}$. Then, the normalized impulse-response signal NS is acquired by synthesizing the low-frequency component derived from the first normalized signal NS1 and the high-frequency component derived from the second normalized signal NS2. Thereafter, the characteristic acoustic-impedance distribution is estimated based on the normalized impulse-response signal NS, and the image data of the characteristic acoustic-impedance image is sequentially constructed, thus eventually obtaining the characteristic acoustic-impedance image. According to this apparatus 1, the first normalized signal NS1 obtained by normalizing the target signal $S_{tgt}$ in the time domain contains the high-frequency component having a low resolution. Nevertheless, only the useful low-frequency component having a small error is extracted, thus removing the above-mentioned unnecessary high-frequency component from said signal. In addition, the second normalized signal NS2 obtained by normalizing the target signal $S_{tgt}$ in the frequency domain contains the low-frequency component and the low-frequency spurious component having a relatively large error. Nevertheless, only the useful high-frequency component having a relatively small error is extracted, thus removing the above-mentioned unnecessary low-frequency spurious component from said signal. Therefore, the useful low-frequency component derived from the first normalized signal NS1 and the useful high-frequency component derived from the second normalized signal NS2 are synthesized to complement the inaccurate parts of both components, thus making it possible relatively easily and surely to acquire a highly reliable normalized impulse-response signal NS. By the way, according to the signal-normalization step as the embodiment of this invention, the unnecessary low-frequency spurious component can be suppressed up to ¹⁄₁₀ or less, as compared with the conventional method for normalizing the signal only in the frequency domain. Furthermore, according to this invention, it is possible to omit the signal-correction processing after the normalization, which has been conventionally required to obtain a desired characteristic acoustic-impedance image. As a result, it is possible to construct a stable characteristic acoustic-impedance image of a very thin skin 8 having a fine internal structure relatively easily and surely without relying on the signal-correction processing after the normalization.

Further, according to the embodiment of this invention, it is possible to construct an ultrasonic tomographic image of a very thin skin 8, having a fine-layered structure, relatively easily and with high accuracy as a characteristic acoustic-impedance image in a fashion that makes it sensuously easy to understand such a layered structure. The characteristic acoustic-impedance image obtained by this apparatus 1 is a visualized image of the cross-sectional distribution (depth distribution) information of the mechanical characteristics of each layer without cutting the target substance (i.e. non-invasively), which is color-coded for each absolute value of the estimated characteristic-acoustic impedance. Therefore, it is sensuously easy to understand the layered structure from this image.

Here, information about the layer within the biological tissue, such as the skin 8 or the like, can be generally obtained from the ultrasonic B-mode echo image obtained by an ordinary ultrasonic-diagnostic apparatus. However, the obtained image is a reflected image from the interface between the layers in which the characteristic-acoustic impedance has a certain amount of difference with each other. In other words, when the difference in the characteristic-acoustic impedance becomes small to some extent, it is not histologically detected even if such an interface exists. Thus, it was extremely difficult to form an image that reflects the structure. That is, a general-reflection image was insufficient to perceive the reflection image (difference in characteristic-acoustic impedance) in which the fine internal structure and the fine layered structure within the biological tissue are reflected. To the contrary, this ultrasonic-image-construction apparatus 1 makes it possible to perceive the layered structure of the skin 8 based on the dynamic-characteristic distribution that was not detected at all by the conventional ultrasonic B-mode echo as a clear tomographic image with sufficient resolution. Further, since such a clear tomographic image could not be acquired by other non-invasive visualization devices (e.g. by optical-coherence tomography (OCT) or by an in-vivo confocal microscope, etc.), it is highly significant that the ultrasonic-image-construction apparatus 1 is now embodied. As described above, according to the ultrasonic-image-construction apparatus 1 as the embodiment of this invention, it is possible easily and non-invasively to evaluate the state of the skin 8 (the state relating to the dynamic characteristics of each layer of the skin 8).

(2) According to the ultrasonic-image-construction apparatus 1 as the embodiment of this invention, in the low-frequency-extraction step, a signal obtained by removing the low-frequency component and the high-frequency component from the spectrum of the second-normalized signal NS2 is used as the source-signal. Then, this source-signal is converted into the time-domain to detect a peak, and a base-signal, having an impulse around the peak, is generated. The base-signal is then used instead of the reference signal $S_{ref}$ to normalize the target signal $S_{tgt}$ in the time-domain. Therefore, compared to the conventional signal-processing method of which the normalization is done in the time-domain without generating the base-signal, the calculation-labor required for the normalization becomes less, thus making it possible to shorten the calculation-time. Therefore, it is possible more easily to acquire a highly reliable normalized-impulse-response signal NS while reducing the burden on the CPU31 as the signal-normalization means.

Also, each embodiment of this invention can be modified, as follows.

Figure 13:
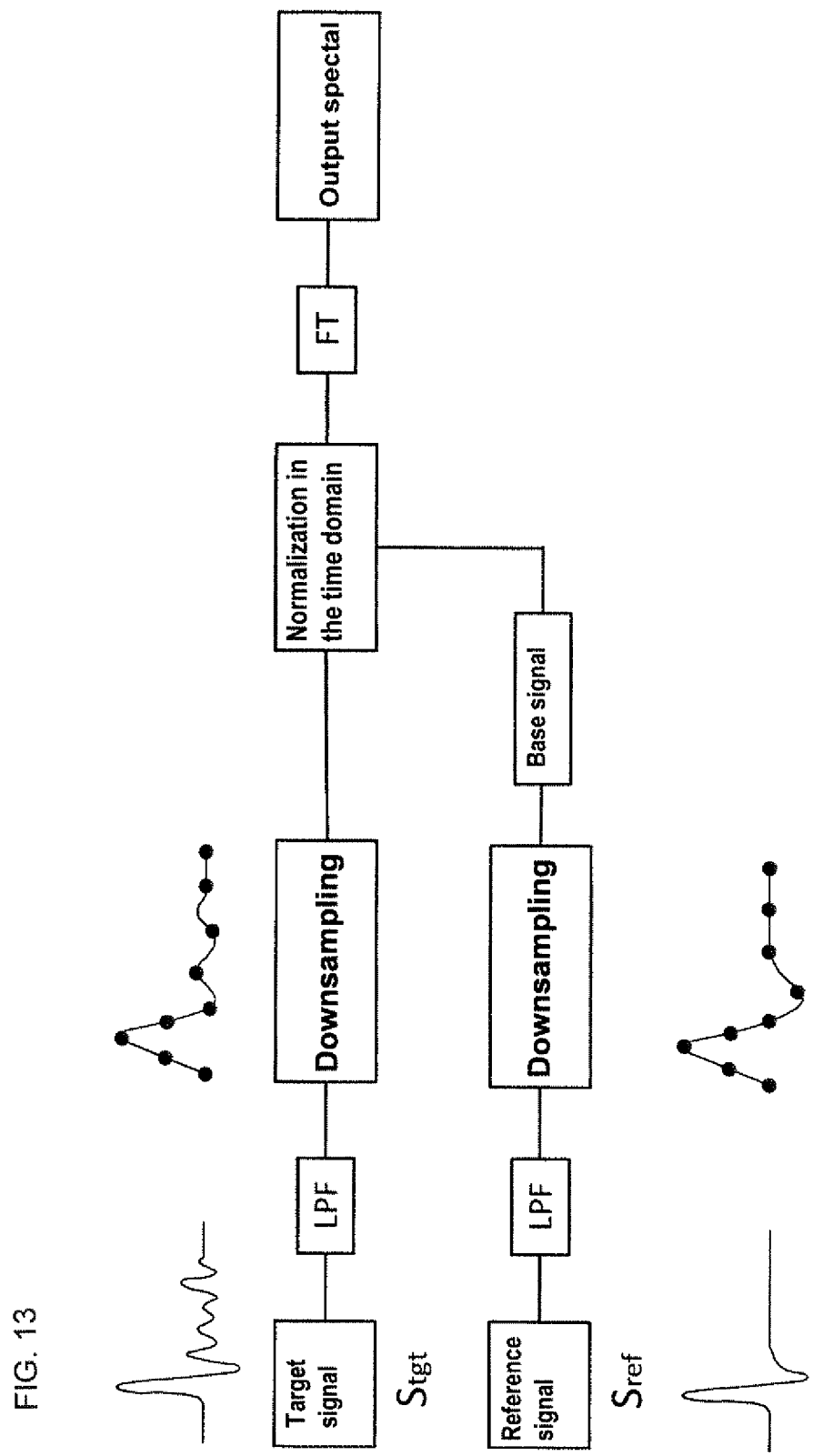
FIG. 13 is a diagram specifically explaining the low-frequency extraction step of the signal-processing method as another embodiment of this invention.
Figure 14:
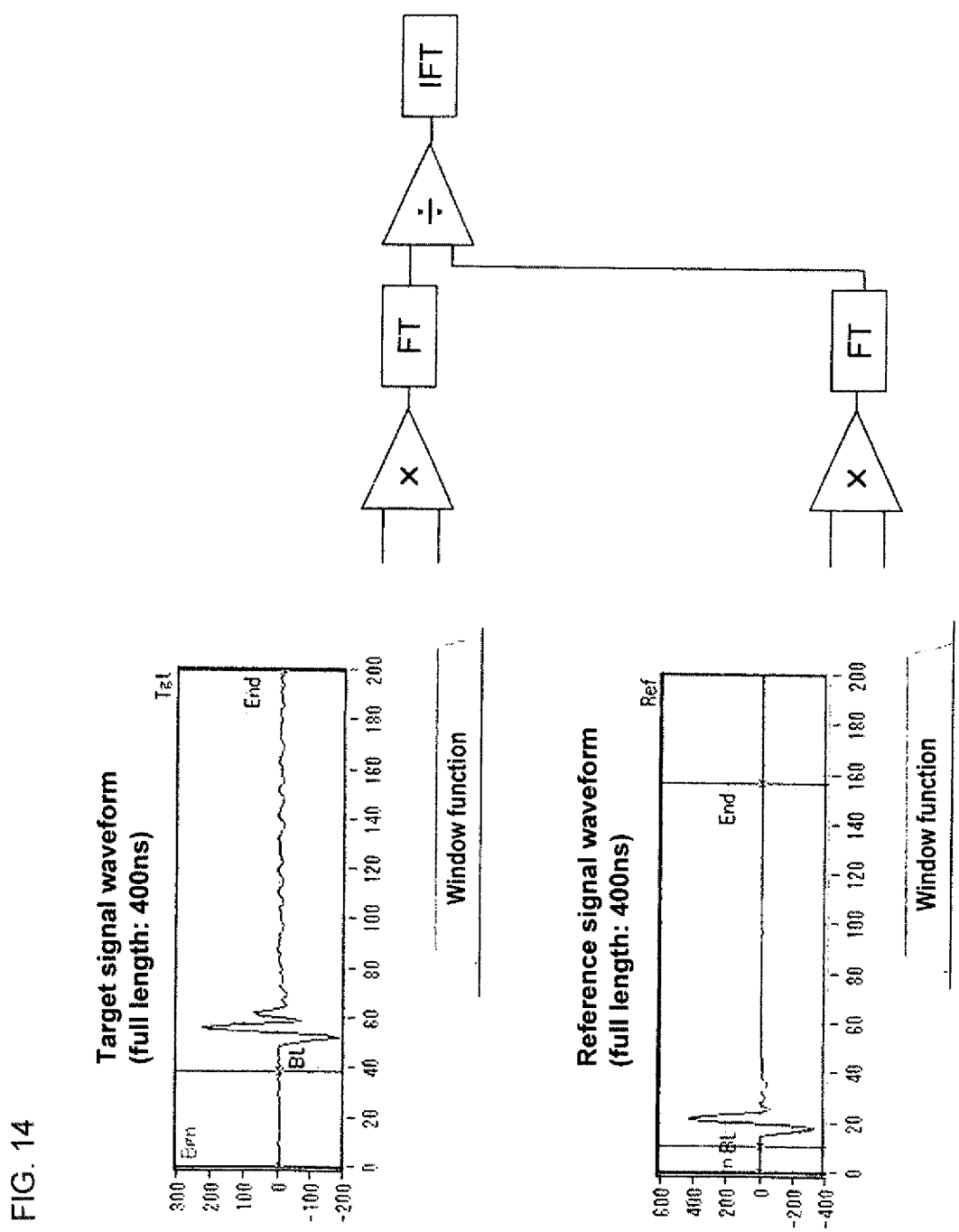
FIG. 14 is a drawing for explaining the problem of the conventional normalization processing in the frequency domain.
Figure 15A:
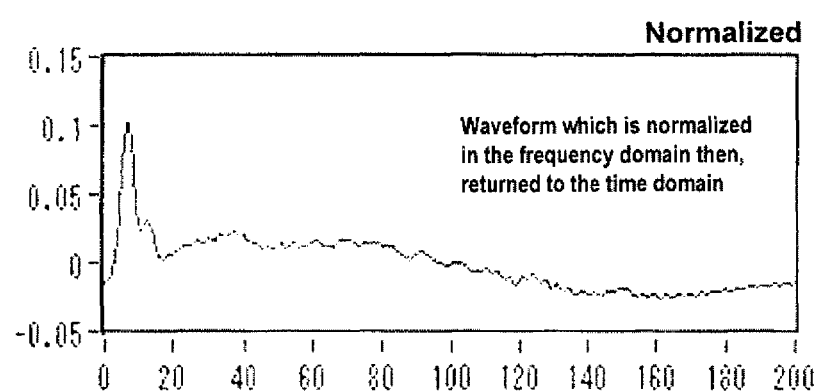
FIGS. 15(a) and 15(b) explain the problem of normalization processing in the conventional frequency domain, with FIG. 15(a) being a drawing showing the time-domain waveform after normalization by which the unnecessary low-frequency spurious component is superimposed over the entire area and FIG. 15(b) being a drawing showing a time-domain waveform that is relatively correctly normalized.
Figure 15B:
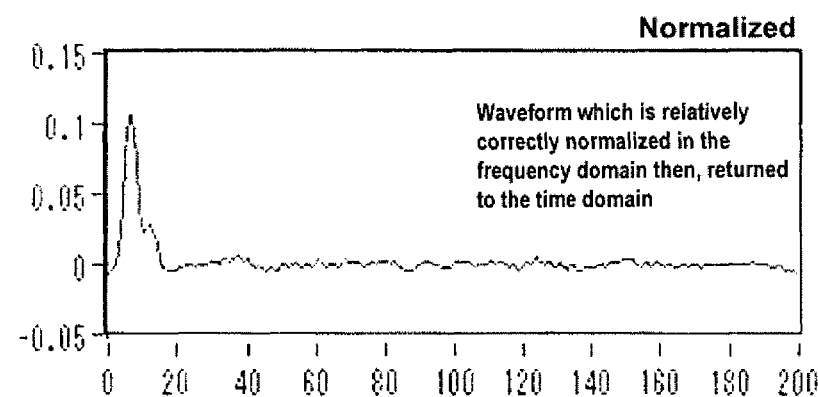

According to the ultrasonic-image-construction apparatus 1 as the above embodiment of this invention, in the low-frequency-extraction step during the signal-normalization step, a predetermined combined base-signal is generated using the signal as the source-signal that is obtained by removing the low-frequency component and the high-frequency component from the spectrum of the second-normalized signal NS2. However, it is not limited to this. The following method can also be applied. For example, as shown in FIG. 13, in the low-frequency-extraction step during the signal-normalization step, the high-frequency component is first removed from the reference signal $S_{ref}$ and target signal $S_{tgt}$, respectively, in the time domain via a low-pass filter (LPF). Then, downsampling is performed to extend the time interval for sampling the data. For this downsampling, the data decimated at sampling points may be directly used, or the average value of data decimated around the sampling points may be used. Using the reference signal $S_{ref}$ after the downsampling process, said signal is shifted at appropriate intervals in the time-axis direction, thus generating some base signals having impulses. Then, as the same as the above-described embodiment, a plurality of base signals are linearly combined using the least-square method, and the combined base signal, thus obtained, is used instead of the reference-signal, thus normalizing the target-signal $S_{tgt}$ after the downsampling process in the time-domain (i.e. reverse-convolution process). According to this method, compared to the conventional signal-processing method for performing the normalization in the time-domain without performing the downsizing, the number of data samples is reduced, so that the calculation-labor required for normalization is also reduced, thus making it possible to shorten the computation-time. Therefore, as the same as the above-described embodiment, it is possible to acquire more easily a highly reliable normalized impulse-response signal NS while reducing the burden on the CPU31 as the signal-normalization means.

According to the ultrasonic-image-construction apparatus 1 as the above-described embodiment, the calculation process is performed using the response signal from the reference member 10 as the reference signal $S_{ref}$. However, it is not limited to this. The reference signal $S_{ref}$ may be a response signal from a location where the skin 8 is not in contact with the upper surface of the resin plate 9. The reflected wave, for example, from a location where the skin 8 and the reference member 10 are not in contact with the upper surface of the resin plate 9 (specifically, the response signal from the surface of the resin plate 9 positioned outside the reference member 10) can also be used. In other words, the response signal from the interface between the resin plate 9 and the air layer may also be used as the reference signal $S_{ref}$.

According to the ultrasonic-image-construction apparatus 1 of the above-described embodiment, ultrasonic waves are irradiated using an inverted-ultrasonic microscope 2 that irradiates ultrasonic waves from below. However, it is also possible to use an upright-ultrasonic microscope that irradiate ultrasonic waves from above.

According to the above-described embodiment, the ultrasonic-image-construction apparatus 1 is used for the purpose of evaluating the condition of the relatively healthy skin 8 that basically has no disease, but the purpose is not limited to this. For example, the ultrasonic-image-construction apparatus 1 can also be used for the purpose of detecting the early stage of skin abnormalities associated with diseases such as skin cancer or the like.

According to the ultrasonic-image-construction apparatus 1 of the above-described embodiment, the target-substance is the human-neck skin 8, but it may of course be the skin 8 of something other than the neck (for example, the cheek or the like). Further, the target-substance does not have to be skin 8, and it may of course be e.g. internal organs, muscles, brain, teeth, nails, surface layer of bone, and the like. Further, the target-substance is not limited to the above-mentioned biological tissue but may be various cultured cells (adherent cells) including e.g. human glial cells. Furthermore, the target-substance does not unnecessarily have to be a biological tissue or an organism but may be a non-living material (e.g. a coating-film, or the like). In other words, the ultrasonic-image-construction apparatus 1 of this invention is not limited to the medical field, the beauty field or the cosmetics field but can also be used in other fields such as the industrial field or the like.

The ultrasonic-image-construction apparatus 1 of the above-described embodiment includes a scanning means for two-dimensionally scanning the ultrasonic transducer 13 with respect to the target-substance, but instead of this, it may include a scanning means for relatively scanning the ultrasonic transducer 13 only in a one-dimensional direction. Further, since the scanning means is not an essential configuration, it may be omitted. As such, the apparatus can be downsized and simplified, thus making it possible to reduce cost.

According to the ultrasonic-image-construction apparatus 1 of the above-described embodiment, the characteristic acoustic-impedance image is constructed based on the estimation result of the characteristic acoustic-impedance distribution in the depth direction, but it is not limited to this. For example, the sound-velocity distribution in the depth direction may be estimated, thus constructing a sound-velocity image based on the result.

The ultrasonic-image-construction apparatus 1 of the above-described embodiment is configured such that a characteristic-acoustic-impedance image is constructed from the reflected-signal sequence that is the source of the ultrasonic B-mode echo image to show it on the display device 36. However, it may of course be configured to show not only the characteristic acoustic impedance image but also the ultrasonic B-mode echo image. Furthermore, it may be configured by incorporating the algorithm of the above embodiment into a general-purpose ultrasonic-diagnostic apparatus that shows an ultrasonic B-mode echo image, thus activating the ultrasonic-image-construction apparatus 1.

In the above-described embodiment, in converting the reflected-signal sequence that is the source of the ultrasonic B-mode echo image into the characteristic acoustic-impedance image in the depth direction, an analysis method that consider multiple reflections in the target-substance is adopted. However, it is not limited to this. For example, when it is considered that the influence of multiple reflections is small, as seen within the biological soft tissue, an analysis method that does not intentionally consider multiple reflections within the target-substance may be adopted.

In the above-described embodiment, the target signal $S_{tgt}$ and the reference signal $S_{ref}$ are obtained by using the ultrasonic pulse as the pulse wave. However, it may also be possible to apply the signal-processing method of this invention in case that the target signal St and the reference signal $S_{ref}$ are obtained by using the pulse of other waves (e.g. electromagnetic waves such as electric waves, light, etc., and sound waves or the like).

DESCRIPTION OF THE REFERENCE NUMERALS

1: Ultrasonic-image-construction apparatus
8: Biological soft tissues (skin) as the target-substance
9: Resin plate as the substrate
10: Reference member as the reference-substance
13: Ultrasonic transducer
31: CPU as the signal-normalization means, characteristic acoustic-impedance-estimation means, image-construction means, and processor
51: Micro-transmission path
$S_{tgt}$: Target signal
$S_{ref}$: Reference signal
NS1: First-normalization signal
NS2: Second-normalization signal
NS: Normalized impulse-response signal

The invention claimed is:

1. An ultrasonic-image construction method comprising:
transmitting and receiving steps in which an ultrasonic pulse is transmitted through a substrate in the state whereof a target substance and a reference substance are in contact with the substrate and in which a target signal from the target substance and a reference signal from the reference substance are received;
a signal-normalization step to extract only a low-frequency component from a first normalized signal obtained by normalizing the target signal in a time domain, and to extract only a high-frequency component from a second normalized signal obtained by normalizing the target signal in a frequency domain using the reference signal, so as to synthesize the low-frequency component derived from the first normalized signal with the high-frequency component derived from the second normalized signal, thus obtaining a normalized impulse signal;
a characteristic acoustic-impedance distribution-estimation step to estimate sequentially a characteristic acoustic-impedance distribution in the target substance from a front side to a back side in a depth direction according to the normalized impulse-response signal; and
an image-construction step to construct image data of an acoustic property image according to the characteristic acoustic-impedance distribution in the depth direction.

2. The ultrasonic-image construction method according to claim 1, characterized in that in the signal-normalization step, before extracting only the high-frequency component from the second normalized signal, a waveform is formed by applying a window function to the reference signal and to the target signal.

3. The ultrasonic-image construction method according to claim 1, characterized in that in the signal-normalization step, the first normalized signal after extracting only the low-frequency component is converted into the frequency domain by Fourier transform.

4. The ultrasonic-image construction method according to claim 1, characterized in that in the signal-normalization step, the low-frequency component derived from the first normalized signal and the high-frequency component derived from the second normalized signal are synthesized in the frequency domain and thereafter an acquired normalized impulse-response signal is converted into the time domain from the frequency domain by inverse Fourier transform.

5. The ultrasonic-image construction method according to claim 1, characterized in that in the signal-normalization step, down-sampling processing is performed after removing the high-frequency component from the reference signal and from the target signal, respectively, thereafter, the target signal, after the down-sampling processing, is normalized in the time domain using the reference signal after the downsampling processing, thus extracting only the low-frequency component from the first normalized signal.

6. The ultrasonic-image construction method according to claim 1, characterized in that in the signal-normalization step, a source signal is obtained by removing the low-frequency component and the high-frequency component from a spectrum of the second normalized signal, thereafter such source signal is converted in the time domain for a peak detection, thereafter a base signal having an impulse is generated around the peak, thus normalizing the target signal in the time domain using the base signal instead of the reference signal, thus extracting only the low-frequency component from the first normalized signal.

7. An ultrasonic-image-construction apparatus comprising:
   a substrate;
   an ultrasonic transducer to transmit an ultrasonic pulse through the substrate in a state where a target substance and a reference substance are in contact with the substrate and which can receive a target signal from the target substance and receive a reference signal from a reference substance;
   a signal-normalization means to extract only a low-frequency component from a first normalized signal obtained by normalizing the target signal in a time domain and to extract only a high-frequency component from a second normalized signal obtained by normalizing the target signal in a frequency domain using the reference signal, so as to synthesize the low-frequency component derived from the first normalized signal with the high-frequency component derived from the second normalized signal, thus obtaining a normalized impulse-response signal;
   a characteristic acoustic-impedance distribution-estimation means to estimate sequentially a characteristic acoustic-impedance distribution in the target substance from a front side to a back side in a depth direction according to the normalized impulse-response signal; and
   an image-construction means to construct image data of an acoustic property image according to an acoustic-impedance distribution in the depth direction obtained by the characteristic acoustic-impedance distribution-estimation means.

8. The ultrasonic-image construction apparatus according to claim 7, characterized in that by the signal-normalization means, before extracting only the high-frequency component from the second normalized signal, a waveform is formed by applying a window function to the reference signal and to the target signal.

9. The ultrasonic-image construction apparatus according to claim 7, characterized in that by the signal-normalization means, the first normalized signal after extracting only the low-frequency component is converted into the frequency domain by Fourier transform.

10. The ultrasonic-image construction apparatus according to claim 7, characterized in that by the signal-normalization means, the low-frequency component derived from the first normalized signal and the high-frequency component derived from the second normalized signal are synthesized in the frequency domain and thereafter the acquired normalized impulse-response signal is converted into the time domain from the frequency domain by inverse Fourier transform.

11. The ultrasonic-image construction apparatus according to claim 7, characterized in that by the signal-normalization means, down-sampling processing is performed after removing the high-frequency component from the reference signal and from the target signal, respectively, thereafter, the target signal, after the down-sampling processing, is normalized in the time domain using the reference signal after the down-sampling processing, thus extracting only the low-frequency component from the first normalized signal.

12. The ultrasonic-image construction apparatus according to claim 7, characterized in that by the signal-normalization means, a source signal is obtained by removing the low-frequency component and the high-frequency component from the spectrum of the second normalized signal, thereafter such source signal is converted in the time domain for a peak detection, thereafter a base signal having an impulse is generated around the peak, thus normalizing the target signal in the time domain using the base signal instead of the reference signal, thus extracting only the low-frequency component from the first normalized signal.

13. A signal-processing method for acquiring a normalized impulse-response signal based on a target signal obtained by pulse-wave irradiation against a target substance, and a reference signal obtained by pulse-wave irradiation against a reference substance, in comprising:
   a low-frequency extraction step to extract only a low-frequency component from a spectrum of a first normalized signal obtained by normalizing the target signal in a time domain;
   a high-frequency extraction step to extract only a high-frequency component from the spectrum of a second normalized signal obtained by normalizing the target signal in a frequency domain using the reference signal; and
   a synthesizing step to synthesize the low-frequency component derived from the first normalized signal and the high-frequency component derived from the second normalized signal, thus acquiring a normalized impulse-response signal.

14. The signal-processing method according to claim 13, characterized in that before performing the high-frequency extraction step, a waveform is formed by applying a window function to the reference signal and to the target signal.

15. The signal-processing method according to claim 13, characterized in that in the low-frequency extraction step, the first normalized signal after extracting only the low-frequency component is converted into the frequency domain by Fourier transform.

16. The signal-processing method according to claim 13, characterized in that in the synthesizing step, the low-frequency component derived from the first normalized signal and the high-frequency component derived from the second normalized signal are synthesized in the frequency domain and thereafter the acquired normalized impulse-response signal is converted into the time domain from the frequency domain by inverse Fourier transform.

17. The signal-processing method according to claim 13, characterized in that in the low-frequency extraction step, down-sampling processing is performed after removing the high-frequency component from the reference signal and from the target signal, respectively, thereafter, the target signal, after the down-sampling processing, is normalized in the time domain using the reference signal after the down-sampling processing.

18. The signal-processing method according to claim 13, characterized in that in the low-frequency extraction step, the source signal is obtained by removing the low-frequency component and the high-frequency component from the spectrum of the second normalized signal, thereafter such source signal is converted in the time domain for a peak detection, thereafter a base signal having an impulse is generated around the peak, thus normalizing the target signal in the time domain using the base signal instead of the reference signal.

* * * * *